US010086372B2

(12) United States Patent
Thompson et al.

(10) Patent No.: US 10,086,372 B2
(45) Date of Patent: Oct. 2, 2018

(54) MEMBRANE-BASED FLUID-FLOW CONTROL DEVICES

(71) Applicant: PRESIDENT AND FELLOWS OF HARVARD COLLEGE, Cambridge, MA (US)

(72) Inventors: Guy Thompson, Watertown, MA (US); Daniel Levner, Boston, MA (US); Christopher David Hinojosa, Cambridge, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 0 days.

(21) Appl. No.: 14/650,735

(22) PCT Filed: Dec. 10, 2013

(86) PCT No.: PCT/US2013/074123
§ 371 (c)(1),
(2) Date: Jun. 9, 2015

(87) PCT Pub. No.: WO2014/133624
PCT Pub. Date: Sep. 4, 2014

(65) Prior Publication Data
US 2015/0306596 A1 Oct. 29, 2015

Related U.S. Application Data

(60) Provisional application No. 61/735,206, filed on Dec. 10, 2012.

(51) Int. Cl.
*B01L 3/00* (2006.01)
*F04B 43/12* (2006.01)
(Continued)

(52) U.S. Cl.
CPC ........ *B01L 3/50273* (2013.01); *F04B 19/006* (2013.01); *F04B 43/12* (2013.01);
(Continued)

(58) Field of Classification Search
CPC ........... B01L 3/50273; B01L 2200/025; B01L 2200/027; B01L 2200/10; B01L 2400/082;
(Continued)

(56) References Cited

U.S. PATENT DOCUMENTS 6,572,349 B2   6/2003  Sorensen et al.
6,581,899 B2 *  6/2003  Williams .............. B01F 5/0646
                                                              251/7
(Continued)

FOREIGN PATENT DOCUMENTS

JP         4312950 B2    8/2009
WO       99/03584 A1    1/1999
(Continued)

OTHER PUBLICATIONS

Gong et al. Wax-bonding 3D microfluidic chips. Lab Chip (2010), v10, p. 2622-2627.*
(Continued)

*Primary Examiner* — Sean C Barron
(74) *Attorney, Agent, or Firm* — Nixon Peabody LLP

(57) ABSTRACT

Described herein are fluid-flow control devices for transferring a fluid from a place to another and/or controlling a fluid flow. In some embodiments, fluid-flow control devices described herein can be used as pumping devices to transfer a fluid by peristaltic motion and/or as valve devices to control fluid flow for various applications, e.g., in a microfluidic platform.

20 Claims, 7 Drawing Sheets

(51) Int. Cl.
  *F04B 19/00* (2006.01)
  *G01N 33/50* (2006.01)
  *C12Q 1/00* (2006.01)
(52) U.S. Cl.
  CPC ... *B01L 2200/025* (2013.01); *B01L 2200/027* (2013.01); *B01L 2200/10* (2013.01); *B01L 2300/0848* (2013.01); *B01L 2300/123* (2013.01); *B01L 2400/0481* (2013.01); *B01L 2400/0655* (2013.01); *B01L 2400/082* (2013.01); *C12Q 1/00* (2013.01); *G01N 33/50* (2013.01)

(58) Field of Classification Search
  CPC ....... B01L 2300/0848; B01L 2300/123; B01L 2400/0481; B01L 2400/065; F04B 43/12; F04B 19/006; F04B 19/00; G01N 33/50; C12Q 1/00
  See application file for complete search history.

(56) References Cited

U.S. PATENT DOCUMENTS

| | | | |
|---|---|---|---|
| 6,602,472 | B1 | 8/2003 | Zimmermann et al. |
| 6,669,454 | B2* | 12/2003 | Lal .................... F04B 17/00 310/321 |
| 7,182,371 | B1 | 2/2007 | Renzi |
| 8,079,836 | B2 | 12/2011 | Gao et al. |
| 2003/0025129 | A1* | 2/2003 | Hahn .................. B01L 3/50273 257/200 |
| 2004/0175298 | A1 | 9/2004 | Choikhet |
| 2011/0287976 | A1 | 11/2011 | Wang et al. |
| 2013/0287613 | A1 | 10/2013 | Gould et al. |

FOREIGN PATENT DOCUMENTS

| | | |
|---|---|---|
| WO | 2010/009307 | 1/2010 |
| WO | 2010/123594 | 10/2010 |
| WO | 2012/048261 A2 | 4/2012 |
| WO | 2013/086502 | 6/2013 |
| WO | 2013/086512 | 6/2013 |
| WO | 2014/039514 | 3/2014 |

OTHER PUBLICATIONS

"Mechanical" Merriam-Webster Online Dictionary (Feb. 2010). (Year: 2010).*

"Couple" Merriam-Webster Online Dictionary (Feb. 2010). (Year: 2010).*

Futai et al. Rapid Prototyping of Microstructures with Bell-Shaped Cross-Sections and its Application to Deforrmation-Based Microfluidic Valves. Advanced Materials (2004), v16(15), p. 1320-1323. (Year: 2004).*

Gu et al. Computerized microfluidic cell culture using elastomeric channels and Braille displays. PNAS (2004), v101(45), p. 15861-15866. (Year: 2004).*

Koch et al. PDMS and tubing-based peristaltic micropumps with direct actuation. Sensors and Actuators B (2009), v135, (Year: 2009) p. 664-670.*

Du M. et al. "A peristaltic micro pump driven by a rotating motor with magnetically attracted steel balls" Sensors 2009, 9, 2611-2620.

Yobas L. et al. "A disposable planar peristaltic pump for lab-on-a-chip" Lab on a Chip 2008, 8, 660-662.

* cited by examiner

MEMBRANE-BASED FLUID-FLOW CONTROL DEVICES

CROSS REFERENCE TO RELATED APPLICATIONS

This application is a 35 U.S.C. § 371 National Phase Entry Application of International Application No. PCT/US2013/074123 filed Dec. 10, 2013, which designates the U.S., and which claims the benefit under 35 U.S.C. § 119(e) of U.S. Provisional Application No. 61/735,206 filed Dec. 10, 2012, the contents of each of which are incorporated herein by reference in their entirety.

GOVERNMENT SUPPORT

This invention was made with government support under Grant No. W911NF-12-2-0036 awarded by Department of Defense/DARPA. The government has certain rights in the invention.

TECHNICAL FIELD

The inventions described herein generally relate to systems or modules thereof used for transferring a fluid from a place to another and/or controlling a fluid flow. In some embodiments, the systems or modules described herein can be used as pumping devices to transfer a fluid by peristaltic motion and/or as valves to control fluid flow in various applications, e.g., in a microfluidic platform.

BACKGROUND

Technologies relating to systems and methods for manipulating minute volumes of fluids, such as biological and chemical fluids, are widely referred to as microfluidics. Microfluidic devices offer the promise of automated analysis with fast reaction times and small sample consumption, and can be used as a platform in various applications, e.g., but not limited to, drug discovery, disease diagnosis, optimization of chemical reactions, in vitro cell culture systems, e.g., organ-on-a-chip devices, life science research, and biological and/or chemical sensor development.

However, controlled fluid transfer in a microfluidic platform is important for all these applications. Some existing microfluidic systems use exterior syringe, diaphragm, or peristaltic devices to induce fluid flow through in the microfluidic network. These systems tend to be much larger in volume than the microfluidic systems they connect to, causing problems with flow control resolution and accuracy. In the case of valves, they often have large (e.g., on the order of 10× or more) swept volume of the systems, resulting in difficulties with separations, mixing, and other microfluidic functions. Accordingly, microdevices and valves, active components sharing the size scale and seamlessly integrated with the rest of the microfluidic system, are desirable.

While examples of microdevices and valves have been developed for microfluidic uses (see, e.g., Yobas et al. "A disposable planar peristaltic device for lab-on-a-chip," *Lab on a Chip* (2008) 8: 660-662; Du et al. "A peristaltic microdevice driven by rotating motor with magnetically attracted steel balls," *Sensors* (2009) 9: 2611-2620), most require complex fabrication and assembly/calibration sequences, e.g., to ensure proper alignment between a microfluidic channel and device elements, such as rolling elements of a peristaltic device, for optimum fluid flow. Accordingly, there is a need in the art for improved microfluidic devices and valves, e.g., with little dead volume that are simple to fabricate and use.

SUMMARY

Embodiments of various aspects described herein relate to fluid-flow control devices that can be used to transfer a fluid and/or control a fluid flow in a conduit for various applications in any working scale. In some embodiments, the fluid-flow control devices described herein can be integrated into microfluidic applications.

The fluid-flow control devices described herein are generally operated by a peristaltic motion to move a fluid through a conduit. However, the fluid-flow control devices described herein are distinct in various aspects from existing peristaltic pumps and/or valves, e.g., the ones described in the International Patent Application No. WO 2012/048261, the content of which is incorporated herein by reference. For example, in some embodiments, the fluid-flow control devices described herein are configured to resolve or mitigate problems of aligning mechanical components such as rolling elements (e.g., ball bearings) precisely with a fluidic channel. In some embodiments, the fluid-flow control devices described herein are configured to prevent rolling elements (e.g., ball bearings) from slipping with respect to a motor, which is in particular a problem for existing valves. In some embodiments, the fluid-flow control devices described herein are configured to address the challenge of properly calibrating the compression force to be applied during a peristaltic motion in order for optimum operation of a peristaltic pump. In some embodiments, the fluid-flow control devices described herein are configured to permit readily services of the devices between uses, while the existing peristaltic pumps and/or valves generally require complicated re-calibration every time when a fluid-contacting component is removed from the pump, e.g., for replacement and/or cleaning. In some embodiments, the fluid-flow control devices are configured to mitigate pulsatile flow of the fluid through the conduit within the device. Accordingly, embodiments of various aspects described herein provide novel fluid-flow control devices that can be performed more efficiently and are more user-friendly than the existing peristaltic pumps and/or valves.

One aspect provided herein is a fluid-flow control device. The fluid-flow control device comprises (a) a substrate layer comprising a deformable portion having a top surface; (b) one or more fluidic conduits disposed in the substrate layer or an adjacent layer, wherein at least one of the fluidic conduit comprises: an inlet portion for receiving a fluid, an outlet portion for outputting the fluid, and a central portion between the inlet portion and the outlet portion; and wherein the central portion comprises a pumping channel; and (c) at least one or any combination of the following features:
  (i) at least one load concentrator that is configured to align and concentrate a load on the pumping channel;
  (ii) the central portion further comprising a roll-off portion, wherein the roll-off portion provides a gradual path for the pressure applying component (e.g., an actuator) to disengage from (or engage with) the pump channel and mitigate the pulsitility of the fluid flow; the roll-off portion, can for example, include a positive effective radius of curvature with respect to the path of the pumping channel; and
  (iii) the top surface of the deformable portion being coupled to at least one rolling element.

In some embodiments, the fluid-flow control device can comprise the feature (i), i.e., the deformable portion including at least one load concentrator. The load concentrator can be designed and positioned to direct the force applied by the actuator on the pumping channel and/or to alleviate the alignment demands between the mechanical components and the deformable portion as required in the existing micropumps. The load concentrator allows the pumping force to be applied to the pumping channel even when the actuator is not precisely aligned with the pumping channel.

In some embodiments, the load concentrator can be formed of a material substantially same as that of the deformable portion.

In some embodiments, the load concentrator can be formed of a material different from that of the deformable portion. For example, the material forming the load concentrator can be less deformable than the material forming the deformable portion. The less deformable material is generally more efficient than a more deformable material in transferring localized loads and forces through the material. Thus, by using a less deformable material for engaging with a pumphead, a lower overall compressive force can be used to create peristalsis of the fluid conduit that makes up the pumping channel and causes the fluid to flow.

In some embodiments, the load concentrator can be formed of a different material than the deformable portion, the deformable material can be selected from a material that has better compatibility and/or is better suited to carry the fluid flowing through the pumping channel, while the load concentrator, which will be in contact with the actuator, can be formed from a more durable and wear resistant material.

In some embodiments, the load concentrator can have a cross-section in any shape, e.g., but not limited to, a circle, a semi-circle, an oval, a rectangle, a square, a polygon, a triangle, an irregular shape, or any combinations thereof. In some embodiments, the load concentrator is a ring.

In some embodiments, the portion of the load concentrator that is engageably in contact with an actuator can have a surface contour conforming to the shape of the contact portion of the actuator.

One or more load concentrators can be placed in any configuration in or on the deformable portion. For example, in some embodiments, at least one load concentrator can be formed on the top surface of the deformable portion. In some embodiments, at least one load concentrator can be formed on the top surface of the deformable portion. In some embodiments, the load concentrator can be formed below the top surface of the deformable portion. For example, at least a portion of the load concentrator can be embedded inside the deformable portion). In some embodiments, at least one load concentrator can be embedded inside the deformable portion, wherein the load concentrator can be placed above or below the fluidic conduit. In general, the load concentrator can be positioned sufficiently adjacent the pumping channel to enable the actuator force to cause a predefined deformation in the shape of the pumping channel and cause the contents of the pumping channel to flow.

In some embodiments, the load concentrator can comprise a protruding surface. As used herein, the term "protruding surface" generally refers to a load concentrator having an outwardly extending surface that extends in to a top surface of the deformable portion. A protruding surface can be angled or curved. For example, in some embodiments, the protruding surface can form or have a cross-section of a circle, a semi-circle (e.g., convex), an oval, a square, a rectangle, a triangle, a polygon, an irregular shape or any combinations thereof.

The dimensions of the load concentrator and/or deformable portion of the substrate layer can vary with the dimensions of the fluidic conduits, which can be suited to needs, e.g., for microfluidic applications vs. non-microfluidic applications. In general, the load concentrator and/or deformable portion of the substrate layer can increase in size with increasing dimensions of the fluidic conduits of the devices described herein. Accordingly, the dimensions of the load concentrator and/or the deformable portion of the substrate layer can range from microns to centimeters. In some embodiments, the height (or thickness) of the load concentrator can range from about 10 µm to about 10 mm, or from about 30 µm to about 6 mm. In one embodiment, the height (or thickness) of the load concentrator can be about 1 mm. In some embodiments, the height (or thickness) of at least the deformable portion of the substrate layer can range from about 10 µm to about 10 mm, or from about 30 µm to about 6 mm. In one embodiment, the height (or thickness) of at least the deformable portion of the substrate layer can be about 1 mm.

In some embodiments, the fluid-contacting part of the fluid-flow control device (e.g., the substrate layer comprising a deformable portion and any adjacent layers) can be detachable from the actuator or the driving element (e.g., a motor). Thus, the fluid-contacting part can be disposable and replaced, if needed, while the actuator or driving element (e.g., a motor) and other mechanics can be reusable. Accordingly, another aspect provided herein is a fluid-flow control device comprising: a substrate layer comprising a deformable portion, the deformable portion having a top surface and including a load concentrator described herein. In some embodiments, the fluid-flow control device can further comprise one or more fluidic conduits disposed in or adjacent to the deformable portion, wherein at least one of the fluidic conduits comprises: an inlet portion for receiving a fluid, an outlet portion for outputting the fluid, and a central portion between the inlet portion and the outlet portion, wherein the central portion comprises a pumping channel.

In various aspects described herein, one or more fluidic conduits can be defined in a separate adjacent substrate layer and/or in the substrate layer of the fluid-flow control device described herein. By way of example only, in some embodiments, the bottom surface of the substrate layer and/or the deformable portion can be affixed to a solid body. The solid body can be rigid or deformable. In some embodiments, at least a portion of the central portion of the fluidic conduit(s) can be defined in a top surface of the solid body. In these embodiments, a portion of the bottom surface of the deformable portion can define the top boundary of the fluidic conduit(s).

In some embodiments, to provide more precise alignment of the deformable portion with mechanical components (e.g., the rolling elements disposed in the actuator), at least a portion of the pumping channel of one or more fluidic conduits can be defined in the deformable portion. In some embodiments, at least a portion of the pumping channel can be defined in the bottom surface of the deformable portion. In these embodiments, a portion of the top surface of the solid body can define the bottom boundary of the pumping channel. In these embodiments, the fluid conduits and the deformable portion of the substrate layer can be manufactured together, so that they are generally well aligned with each other. Additionally or alternatively, at least a portion of the pumping channel can be defined between the top and bottom surfaces of the deformable portion.

In some embodiments, a first sub-channel can be defined in the bottom surface of the deformable portion and a second sub-channel can be defined in the top surface of a solid body. In these embodiments, a fluidic conduit can be formed by aligning the first sub-channel with the second sub-channel such that the first sub-channel provides a top boundary of the resultant fluidic conduit and the second sub-channel provides a bottom boundary of the resultant fluidic conduit.

In accordance with some embodiments of the invention, the fluid-flow control device can comprise the feature (ii), i.e., the central portion of the fluidic conduits further comprising a roll-off portion, wherein the roll-off portion provides a gradual path for the pressure applying component (e.g., an actuator) to disengage from (or engage with) the pump channel and mitigate the pulsatility of the fluid flow. In accordance with some embodiments of the invention, the central portion of the fluidic conduits further comprises a first roll-off portion, wherein the first roll-off portion provides a gradual path for the actuator to engage the pump channel and mitigate the pulsatility of the fluid flow at the inlet and a second roll-off portion, wherein the second roll-off portion provides a gradual path for the actuator to disengage the pump channel and mitigate the pulsatility of the fluid flow at the outlet. In accordance with some embodiments of the invention, the roll-off portion can include a positive effective radius of curvature or local radius of curvature with respect to the path and/or curvature of the pumping channel. In accordance with some embodiments of the invention, the roll-off portion can be located between the pumping channel and the outlet portion. In accordance with some embodiments of the invention, the roll-off portion can be located between the pumping channel and the inlet portion. In accordance with some embodiments of the invention a first roll-off portion can be located between the pumping channel and the outlet portion and a second roll-off portion can be located between the inlet portion and the pumping channel. In accordance with some embodiments of the invention, the path of the roll-off portion is designed to gradually extend outside of a region of compression such that during operation, rolling elements can be disengaged from (or engaged with) the corresponding fluid conduit gradually, thereby mitigating pulsatile flow generated otherwise. In accordance with some embodiments of the invention, the path of the roll-off portion is designed to gradually extend inside of a region of compression such that during operation, rolling elements can be disengaged from (or engaged with) the corresponding fluid conduit gradually, thereby mitigating pulsatile flow generated otherwise.

In some embodiments, the fluid-flow control device can further comprise an actuator that engages and applies pressure on the deformable portion. As the actuator applies a pressure to the deformable portion, the pumping channel disposed therein is deformed, thereby forcing a fluid to move through the central portion from the inlet portion to the outlet portion.

In some embodiments, the actuator can further comprise at least one rolling element and/or at least one low friction material. For example, the rolling element(s) and/or the low friction material can be mechanically connected to a shaft fixed to the actuator. Such embodiments of the fluid-flow control device can prevent bearing-slip problems encountered by the existing peristaltic pumps and/or valves.

Any types of art-recognized rolling elements, e.g., to provide a compressive force to a deformable portion, can be utilized in the fluid-flow control devices described herein. Examples of rolling elements can include, but are not limited to, ball bearings, plain bearings (e.g., but not limited to, sleeve bearings), roller bearings (e.g., but not limited to, cylindrical rollers, rounded (convex) rollers, needles, tapered rollers, and spherical rollers) or any combinations thereof. The shape of the rolling elements can vary, for example, with the design of the actuator and/or load concentrator. In some embodiments, the rolling elements can be cylindrical, tapered, convex, spherical, irregular-shaped, or any combinations thereof.

In some embodiments, the actuator can comprise at least one low friction material capable of sliding against the deformable portion of the substrate layer. Examples of such low friction materials can include, but are not limited to, polytetrafluoroethylene (PTFE), acetal, DELRIN®, RULON®, CELCON®, HOSTAFORM®, and any combinations thereof.

In some embodiments, the actuator can further comprise a driving element, e.g., a motor. While a driving element, e.g., a motor, can be integrated into the actuator, in some embodiments, the actuator can be mechanically connected to a driving element, e.g., a motor such that at least a portion of the actuator can be detachable from the driving element, e.g., a motor, if needed. For example, the actuator can comprise a detachable mechanical connector and/or adaptor, e.g., a motor shaft slot, to provide detachable mechanical connection with a driving element, e.g., a motor.

Existing peristaltic pumps and/or valves generally comprise non-disposable mechanical parts (e.g., but not limited to, driving elements such as motors, and rolling elements) and fluid-contacting parts integrated together in one assembly. Thus, there is no simple way to dispose of the fluid-contacting portion of the pumps while retaining the motor/mechanics without re-calibration. Accordingly, in some embodiments of the invention, the fluid-flow control device is configured to provide easy serviceability, e.g., the fluid-contacting component can be readily replaced. For example, the actuator (comprising mechanical components, e.g., but not limited to, rolling elements and/or driving elements (e.g., a motor)) and the substrate layer (fluid-contacting part) of the fluid-flow control device described herein can be configured to be detachable from each other. In these embodiments, the fluid-flow control device can further comprise a latch and/or a lever to secure the substrate layer and the actuator together when the device is in use. In some embodiments, the substrate layer comprising the deformable portion can be disposable.

In some embodiments, the actuator can further comprise an elastic element mechanically coupled to at least one rolling element. The elastic element (e.g., but not limited to, a spring or flexure) can be selected such that a small variation in displacement of the elastic element does not correspond to a large deviation in force. Thus, the presence of such elastic element can provide a better control of the compressive force to the deformable portion of the substrate layer, even in the absence of calibration prior to use.

For example, in some embodiments, the elastic element can include a spring or any functional equivalent thereof. In some embodiments, the spring can be pre-compressed such that the spring can be ready to provide a desired effectively near-constant force as soon as the deformable portion of the substrate layer comes into contact with the rolling elements and/or low-friction materials. Any art-recognized methods used to pre-compress a spring can be integrated into the fluid-flow control devices described herein. By way of example only, the spring can be pre-compressed by mechanically connecting to a rod structure (e.g., but not limited to, a shoulder bolt) such that the rod structure pre-compresses spring.

In alternative embodiments, a flexure, e.g., the substrate layer and/or the solid body itself, can be sufficiently flexible, and can thus be used as an elastic element, for example, in place of a spring element.

While in some embodiments, the rolling element(s) can be integrated into the actuator, which are then brought into contact with the deformable portion during operation, in alternative embodiments, the top surface of the deformable portion of substrate layer (or the top surface of the load concentrator if extending from the top surface of the deformable portion) can be configured to be in pre-contact with at least one rolling element described herein. Accordingly, in some embodiments, the fluid-flow control device can comprise the feature (iii), i.e., the top surface of the deformable portion or the top surface of the load concentrator being coupled to at least one rolling element. This feature forms a "snap-on rolling element" for plug-and-play applications. For example, these embodiments can be desirable for use as valves because it can retain the fluidic configuration even when it is not engaged with an actuator or a driving element (e.g., a motor). In these embodiments, the rolling element(s) can be configured to be engageable with part of the actuator that is detachable from a driving element (e.g., a motor). In some embodiments, the rolling element(s) can be mechanically connected to a shaft fixed to the actuator, e.g., to prevent bearing-slip problem as described above.

In some embodiments, the fluid-flow control device can comprise at least two of the features (i)-(iii) in any combination. In some embodiments, the fluid-flow control device can comprise all of the features (i)-(iii).

In various aspects described herein, the fluid-flow control devices can be configured to have fluidic conduits of different sizes, depending on types and/or nature of applications (e.g., microfluidic or low-volume fluid flow applications vs. non-microfluidic or high-volume fluid flow applications). Without wishing to be bound by theory, larger fluidic conduits of the devices described herein can be generally used for higher desirable volume of fluid flow or fluid to be transferred, and smaller fluidic conduits for lower desirable volume of fluid flow or fluid to be transferred. In some embodiments, the fluid-flow control devices are configured for microfluidic applications, e.g., for fluid transfer and/or delivery in a microfluidic platform such as a microfluidic device. Accordingly, in some embodiments, at least one of the fluidic conduits configured to be in contact with the deformable portion of the substrate layer can comprise a microfluidic channel.

The fluidic conduit(s) can have a cross-section of any shape, e.g., rectangular, square, circle, semi-circle, oval, polygon, irregular-shaped, or any combinations thereof. In some embodiments, the fluidic conduit(s) can be configured to reduce the compression force needed to effect pumping and/or valving, e.g., to reduce leakage of a fluid. For example, in some embodiments, at least one of the fluidic conduits can have a semi-circular cross-section, e.g., forming at least one rounded surface. In some embodiments, at least one of the fluidic conduits can comprise a surface forming a contact angle of about 50 degrees to about 70 degrees relative to another surface that defines a boundary of the fluidic conduit. In one embodiment, at least one of the fluidic conduits can comprise a surface forming a contact angle of about 60 degrees relative to another surface that defines a boundary of the fluidic conduit.

The fluidic conduits(s) can be defined and arranged in the substrate layer and/or solid body in any pattern, e.g., linear, circular, spiral, rectangular, polygonal, irregular-shaped, or any combinations thereof.

In operation, as the actuator engages with the deformable portion of the substrate layer (e.g., by applying a varying force or pressure to the deformable portion or the load concentrator, if any), the deformable portion of the substrate layer can deform, which in turn changes the volume of the underlying fluidic conduit(s), thereby controlling the volume of a fluid flowing through the fluidic conduit(s). In some embodiments, the fluid-flow control device can be used as a pumping device, e.g., to force a fluid inside the fluidic conduit(s) moving through the central portion from the inlet to the outlet. In some embodiments, the fluid-flow control device can be used as a valve to control a fluid flow through a fluidic conduit.

In another aspect, one or any combinations of the features (i)-(iii) described herein can be incorporated in the micropumps and/or microvalves described in the International Patent Application No. WO 2012/048261, the content of which is incorporated herein by reference.

BRIEF DESCRIPTION OF THE DRAWINGS

The foregoing summary, as well as the following detailed description of the present disclosure, will be better understood when read in conjunction with the appended drawings. For the purpose of illustrating the present disclosure, there are shown in the drawings embodiments. It should be understood, however, that the present disclosure is not limited to the precise arrangements and instrumentalities shown.

FIG. 2A is a cross-sectional view of a rectangular load concentrator over a channel (e.g., a square channel). FIG. 2B is a cross-sectional view of a polygonal load concentrator over a channel (e.g., a square channel). FIG. 2C is a cross-sectional view of an irregular-shaped load concentrator over a channel (e.g., a square channel).

FIG. 3A shows a channel (e.g., a square channel) defined in the bottom surface of the deformable portion while a portion of the top surface of the solid body defines the bottom boundary of the channel. FIG. 3B shows a channel (e.g., a square channel) formed by aligning a first sub-channel with a second sub-channel, wherein the first sub-channel is defined in the bottom surface of the deformable portion and the second sub-channel is defined in the top surface of the solid body. FIG. 3C shows a channel (e.g., a square channel) defined in the top surface of the solid body while a portion of the bottom surface of the deformable portion defines the top boundary of the channel. FIG. 3D shows a channel (e.g., a square channel) defined between the bottom surface and the top surface of the deformable portion.

FIG. 9A shows that a load concentrator is formed on the top surface of the substrate layer comprising a deformable portion and a fluidic conduit, wherein the fluidic conduit is disposed in the deformable portion. FIG. 9B shows that a load concentrator is molded into the substrate layer or the substrate layer is molded around the load concentrator. FIG. 9C shows that one or more load concentrators embedded into the deformable portion of the substrate layer. The geometries of the cross-section of the load concentrator shown in FIGS. 9A-9C are for illustration of examples and are not intended to be limiting, as other geometries can also fall within the scope of the invention. In both FIGS. 9A-9C, the load concentrator and the deformable portion can be formed of materials of different elasticities or hardness. For example, the load concentrator can be formed of a material that is less deformable than the material forming the deformable portion of the substrate layer. As a less-deformable material is generally more efficient in propagating an applied pressure to deform the deformable portion of the substrate layer, a lower compression force can be used to create a peristalsis of a fluid flow. Further, the less-deformable material can be more durable and resistant to wear due to friction and allow the deformable portion to be selected for more optimum fluid compatibility and flow.

FIG. 10A shows a linear ROP. FIG. 10B shows a ROP with a positive radius of curvature with respect to the path and/or curvature of the pumping channel.

DETAILED DESCRIPTION OF THE INVENTION

Figure 1:
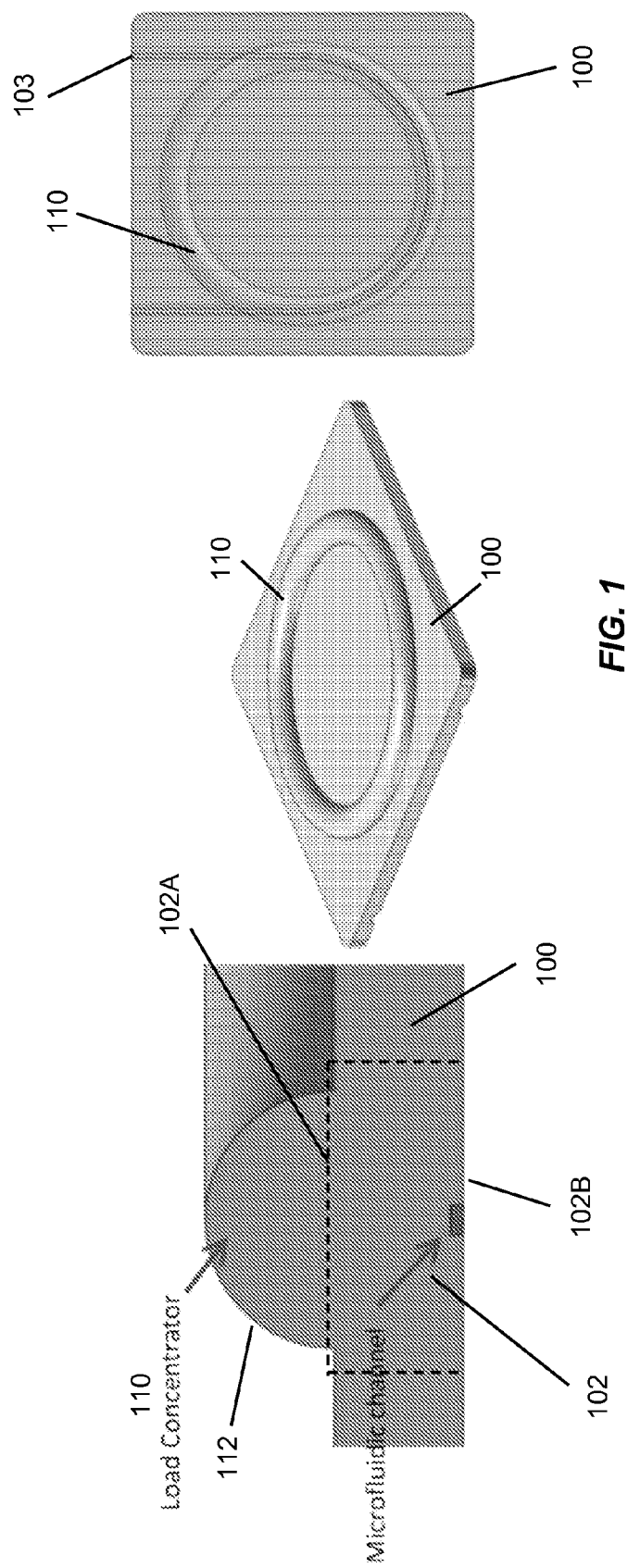
FIG. 1 is a set of schematic representations showing a load concentrator formed on the top surface of an elastomeric membrane over a microfluidic channel defined in the bottom surface of the elastomeric membrane. The left panel is a cross-sectional view of a semi-circular load concentrator over a square channel. The center panel is a 3-D perspective view of a pump's or valve's elastomeric manifold showing a circular-shaped load concentrator. The right panel is a transparent top view of the manifold (shown in the middle panel), showing the microfluidic channel underlying the load concentrator.
Figure 2A:
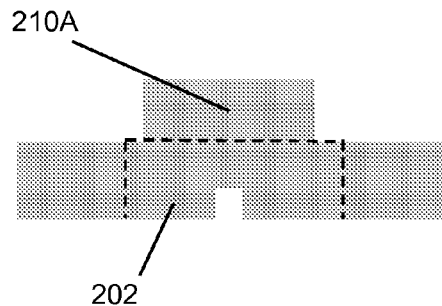
FIGS. 2A-2C are schematic representations showing cross-sectional views of various forms of load concentrators.
Figure 2B:
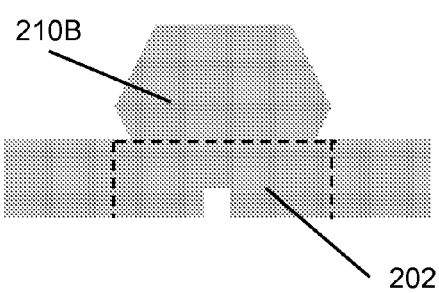
Figure 2C:
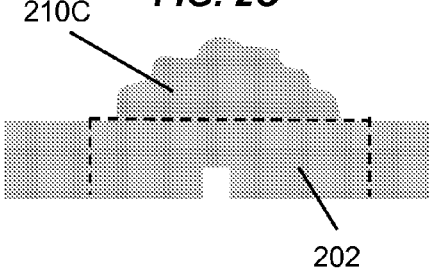

Existing peristaltic pumps and/or valves, e.g., micropumps and/or microvalves for use in microfluidic applications, have suffered from, e.g., problems of alignment between the mechanical bearing components and fluidic conduits; and/or bearing-slip problems. In addition, the existing peristaltic pumps and/or valves need to be calibrated individually to attain the correct compression of the bearings against the fluidic conduits, and/or replacing the fluid-contacting portion of the existing pumps after use requires tools and subsequent re-calibration. Accordingly, there is a need for development of an improved pump and/or valve that can resolve at least one or more of the aforementioned problems.

Embodiments of various aspects described herein relate to fluid-flow control devices that can be used to transfer a fluid and/or control a fluid flow in a conduit for various microfluidic and non-microfluidic applications. In some embodiments, the fluid-flow control devices described herein can be integrated into microfluidic applications. The fluid-flow control devices described herein are generally operated by a peristaltic motion to move a fluid through a conduit, and are configured to address at least one or more of the aforementioned problems associated with the existing peristaltic pumps and/or valves, e.g., the ones described in the International Patent Application No. WO 2012/048261, the content of which is incorporated herein by reference.

One aspect provided herein is a fluid-flow control device. The fluid-flow control device comprises (a) a substrate layer comprising a deformable portion having a top surface; (b) one or more fluidic conduits disposed in the deformable portion, wherein at least one of the fluidic conduit comprises: an inlet portion for receiving a fluid, an outlet portion for outputting the fluid, and a central portion between the inlet portion and the outlet portion; and wherein the central portion comprises a pumping channel; and (c) at least one or any combination of the following features:
  (i) the deformable portion including at least one load concentrator that is configured to align and concentrate a load applied to the deformable portion on the pumping channel;
  (ii) the central portion further comprising a roll-off portion, wherein the roll-off portion provides a gradual path for the pressure applying component (e.g., an actuator) to disengage from (or engage with) the pump channel and mitigate the pulsatility of the fluid flow; the roll-off portion, can for example, include a positive effective radius of curvature with respect to the path of the pumping channel; and
  (iii) the top surface of the deformable portion being coupled to at least one rolling element.

As used herein, the term "substrate layer" refers to a base material comprising at least one or more deformable portions. In some embodiments, the entire substrate layer can be a deformable base material. As used herein, the term "deformable" generally refers to a material being capable of bending or flexing such that it is pliant and yieldable in response to a change in surrounding condition (e.g., an applied pressure or force), without causing any macroscopic breaking. A deformable material can generally alter geometric shape, e.g., bending, and structure to accommodate a change in surrounding condition and to conform to the shape of an object brought in contact with it without losing its integrity.

In some embodiments, the substrate layer can comprise at least one or more (including, e.g., at least two or more, at least three or more) individual deformable portions. Each deformable portion can independently comprise one or more fluidic conduits disposed therein. In some embodiments, some deformable portions can each independently comprise one or more fluidic conduits disposed therein. In these embodiments, same or different compressive forces can be independently applied to each individual deformable portion, thus independently altering the flow rates of at least some fluidic conduits. In alternative embodiments, some deformable portions can each independently comprise more than one fluidic conduit (e.g., 2 or more fluidic conduits). In these embodiments, depending on, e.g., the sizes of the fluidic conduits, the fluidic conduits disposed in the same deformable portion can have the same or different flow rates.

At least the deformable portion of the substrate layer can be fabricated from any elastomeric material. In some embodiments, the substrate layer (or the base material) can be also fabricated from an elastomeric material. In some embodiments, the substrate layer can be fabricated from the same elastomeric material as the fabrication material of the deformable portion, e.g., for ease of massive manufacture. In some embodiments, the substrate layer can be fabricated from an elastomeric material different from the fabrication material of the deformable portion. As used herein, the term "elastomeric material" or "elastomer" refers to a polymeric material having low Young's modulus and high yield strain compared with other types of polymeric materials. The elastomeric materials can be moldable and/or curable. In some embodiments, the elastomeric material can include rubber. Exemplary flexible and/or elastomeric materials that can be used for fabrication of the substrate layer and/or the deformable portion can include, without limitations, polydimethylsiloxane (PDMS), polyurethane, rubber, gels, hydrogels, molded plastic, polymethylmethacrylate (PMMA), polycarbonate, polytetrafluoroethylene (TEFLON™), polyvinylchloride (PVC), polysulfone, mixture of hydrocarbon oils, polymers containing plasticizers, synthetic polyisoprene, polybutadiene, chloroprene rubber, polychloroprene, neoprene, baypren, butyl rubber (e.g., copolymer of isobutylene and isoprene), halogenated butyl rubbers (e.g., chloro butyl rubber; bromo butyl rubber), styrene-butadiene rubber (copolymer of styrene and butadiene), styrene-ethylene/butadiene-styrene (SEBS), nitrile rubber (copolymer of butadiene and acrylonitrile), hydrogenated nitrile rubbers, ethylene propylene rubber, ethylene propylene diene rubber, epichlorohydrin rubber, polyacrylic rubber, silicone rubber, fluorosilicone rubber, fluoroelastomers, perfluoroelastomers, polyether block amides, chlorosulfonated polyethylene, ethylene-vinyl acetate, and any combinations thereof.

In some embodiments, materials selected for fabricating the deformable portion and/or at least one fluidic conduit can be biocompatible. By the term "biocompatible material" meant is a naturally-occurring or synthetic material which when in contact with a biological cell does not provoke an adverse response in the cell. In some embodiments, the biocompatible material does not contain any plasticizers. In some embodiments, the biocompatible material does not absorb any of the components of the fluid or permit the components to adhere to the surface of the fluidic conduit. Examples of biocompatible polymers include, but are not limited to, silicone and silicone-based polymers (e.g., polydimethylsiloxane (PDMS)); liquid silicone rubber; polymethylmethacrylate (PMMA), styrene-ethylene/buradiene-styrene (SEBS), polyurethane, styrenic block copolymers, polytetrafluoroethylene (PTFE); a natural or synthetic hydrogel; polysulfone; polyethylene; polycarbonate, polypropylene; polyamide; polyester; polymethylmethacrylate, polylactic acid (PLA), polyglycolic acid (PGA), poly(lactic-co-glycolic acid) (PLGA), any art-recognized biocompatible polymers, and any combinations thereof. Examples of polyurethane include, but are not limited to, thermoplastic polyurethane elastomers (e.g., but not limited to Texin® and Desmopan® by Bayer, Bionate® by the Polymer Technology Group), as well as ether-based, aliphatic polyurethane disclosed in the International Pat. App. No. PCT/US12/36920 filed May 8, 2012, the content of which is incorporated herein by reference in its entirety.

In some embodiments, materials selected for at least the deformable portion of the substrate layer can be elastomeric and biocompatible material. An exemplary elastomeric and biocompatible material includes PDMA (e.g., Sylgard 184).

In some embodiments, materials selected for at least the deformable portion of the substrate layer can have an elastic modulus or Young's modulus (measured at room temperature) of about 0.1 MPa to about 5 MPa, about 1 MPa to about 500 MPa, about 1.5 MPa to about 3 MPa, or about 1.5 MPa to about 2 MPa. In some embodiments, the material selected for at least the deformable portion or the substrate layer can have an elastic modulus or Young's modulus (measured at room temperature) of about 1.5 MPa to about 2 MPa.

In some embodiments, materials selected for at least the deformable portion of the substrate layer can be a soft elastomer. Without wishing to be bound by theory, Shore A scale is generally used for testing soft elastomers, while hardness of hard elastomers can be measured by Shore D scale. Shore (durometer) hardness test are known in the art and the hardness values can be converted between two different scales. For example, a Shore A value of 55 is equivalent to a Shore D value of about 14. In some embodiments, the soft elastomer selected for at least the deformable portion or the substrate layer can have a hardness value (based on a Shore A scale) of about 30 to about 70, or about 35 to about 60, or about 40 to about 66. In some embodiments, the soft elastomer selected for at least the deformable portion or the substrate layer can have a hardness value (based on a Shore A scale) of no more than 70, no more than 60, no more than 50, or no more than 40. In some embodiments, the soft elastomer selected for at least the deformable portion or the substrate layer can have a hardness value (based on a Shore A scale) of about 50 to about 60. In some embodiments, the soft elastomer selected for at least the deformable portion or the substrate layer can have a hardness value (based on a Shore A scale) of about 55.

Dimensions of the substrate layer and/or deformable portion of the substrate layer can vary with dimensions of the fluidic conduits disposed in the deformable portion. In general, a larger deformable portion of the substrate layer is desired to accommodate a larger fluidic conduit. Accordingly, the dimensions of the deformable portion of the substrate layer can range from microns to centimeters, e.g., depending on types of applications (e.g., microfluidic vs. non-microfluidic applications). For example, in some embodiments, the height (or thickness) of at least the deformable portion of the substrate layer and/or the rest of the substrate layer can range from about 10 µm to about 30 mm, or from about 20 µm to about 20 mm, or from about 30 µm to about 10 mm. In one embodiment, the height (or thickness) of at least the deformable portion of the substrate layer and/or the rest of the substrate layer can be about 1 mm. In some embodiments, e.g., for microfluidic applications, the height (or thickness) of at least the deformable portion of the substrate layer and/or the rest of the substrate layer can range from about 10 µm to about 1000 µm, or from about 20 µm to about 900 µm, or from about 30 µm to about 800 µm, or from about 40 µm to about 700 µm, or from about 50 µm to about 600 µm, or from about 100 µm to about 500 µm. In some embodiments, e.g., for non-microfluidic applications, the height (or thickness) of at least the deformable portion of the substrate layer and/or the rest of the substrate layer can range from about 1 mm to about 50 mm, or from about 5 mm to about 40 mm, or from about 10 mm to about 30 mm.

In some embodiments, the fluid-flow control device can comprise at least two of the features (i)-(v) as shown in Table 1 below. In some embodiments, the fluid-flow control device can comprise at least three of the features (i)-(v). In some embodiments, the fluid-flow control devices can comprise at least four of the features (i)-(v). In one embodiment, the fluid-flow control device can comprise all of the features (i)-(v). In some embodiments, the fluid-flow control device can be configured to comprise any one of the combinations shown in Table 1. The symbol "x" indicates the presence of a feature in a combination. Each of the features (i) to (v) is further described in detail below.

features (ii)-(v). In some embodiments, a fluid-flow control device can comprise the feature (i) of the load concentrator and the feature (iv) of the rolling elements (e.g., but not limited to rollers) and/or low friction material.

In some embodiments, a fluid-flow control device can comprise no feature (i) of the load concentrator (e.g., using a flat deformable portion instead), but can comprise the feature (iv), e.g., using one or more rounded (convex) rollers, which can emulate typical ball bearings but without associated slip problem. In these embodiments, the fluid-flow control device can further optionally comprise an elastic element (feature (v)).

In some embodiments, a fluid-flow control device can comprise no feature (i) of the load concentrator (e.g., using a flat deformable portion instead), but can comprise the feature (iii) of snap-on rolling elements. In some embodiments, the snap-on rolling elements can comprise rounded (convex) rollers, and can further optionally comprise an elastic element (feature (v)).

In some embodiments, any one of the combinations shown in Table 1 and any embodiments described herein can be incorporated in micropumps and/or microvalves described in the International Patent Application No. WO

TABLE 1

Exemplary embodiments of fluid-flow control devices comprising various combinations of features (i) to (v).

| Combination | Feature (i):<br>Load concentrator | Feature (ii):<br>Roll-Off Portion | Feature (iii):<br>Snap-on rolling elements | Feature (iv): Rolling elements and/or low friction material | Feature (v):<br>Elastic Elements |
|---|---|---|---|---|---|
| 1 | x | | | | |
| 2 | | x | | | |
| 3 | | | x | | |
| 4 | | | | x | |
| 5 | | | | | x |
| 6 | x | x | | | |
| 7 | x | | x | | |
| 8 | x | | | x | |
| 9 | x | | | | x |
| 10 | | x | x | | |
| 11 | | x | | x | |
| 12 | | x | | | x |
| 13 | | | x | x | |
| 14 | | | x | | x |
| 15 | | | | x | x |
| 16 | x | x | x | | |
| 17 | x | x | | x | |
| 18 | x | x | | | x |
| 19 | x | | x | x | |
| 20 | x | | x | | x |
| 21 | x | | | x | x |
| 22 | | x | x | x | |
| 23 | | x | x | | x |
| 24 | | x | | x | x |
| 25 | | | x | x | x |
| 26 | x | x | x | x | |
| 27 | x | x | x | | x |
| 28 | x | x | | x | x |
| 29 | | x | x | x | x |
| 30 | x | | x | x | x |
| 31 | x | x | x | x | x |

In some embodiments, a fluid-flow control device can comprise the feature (i) of the load concentrator. The load concentrator can use the same material as or a different material from the material used in the deformable portion of the substrate layer. In these embodiments, the fluid-flow control device can further comprise any combinations of the 2012/048261, the content of which is incorporated herein by reference.

In some embodiments, the fluid-flow control device can further comprise an actuator that engages and applies pressure on the deformable portion. As the actuator applies a pressure to the deformable portion, the pumping channel disposed therein is deformed, thereby forcing a fluid to move through the central portion from the inlet portion to the outlet portion.

In some embodiments, the actuator can further comprise at least one rolling element and/or at least one low friction material, which will be discussed in detail below. For example, the rolling element(s) and/or the low friction material can be mechanically connected to a shaft fixed to the actuator. Such embodiments of the fluid-flow control device can prevent bearing-slip problems encountered by the existing peristaltic pumps and/or valves.

In operation, as the actuator engages with the deformable portion of the substrate layer (e.g., by applying a varying force or pressure to the deformable portion or the load concentrator, if any), the deformable portion of the substrate layer can deform, which in turn changes the volume of the underlying fluidic conduit(s), thereby controlling the volume of a fluid flowing through the fluidic conduit(s). Depending on, for example, the material of the deformable portion, the load concentrator, and/or size of the pumping channel, the compressive load used to compress the pumping channel can vary accordingly. For example, in some embodiments, the compressive load is sufficient to compress between 10% and up to 100% of the pumping channel volume. In some embodiments, the compressive load is sufficient to compress at least about 50% of the pumping channel volume. In some embodiments, the compressive load can be about 0.1 lbf to about 10 lbf, about 0.5 lbf to about 7 lbf, or about 1 lbf to about 5 lbf.

In some embodiments, the fluid-flow control device can be used as a pumping device, e.g., to force a fluid inside the fluidic conduit(s) to move through the central portion from the inlet to the outlet. In some embodiments, the fluid-flow control device can be used as a valve to control a fluid flow through a fluidic conduit that connects an inlet to an outlet.

Fluidic Conduits

In embodiments of some aspects described herein, one or more fluidic conduits are disposed in a deformable portion of a substrate layer. As used herein, the term "fluidic conduits" generally refers to channels, ducts, tubes, or pathways through and along which a fluid (e.g., gas or liquid) can flow, pass or move. Each fluidic conduit described herein can comprise an inlet portion (e.g., a port and/or a pathway for introduction of a fluid), an outlet portion (e.g., a port and/or a pathway for exit of the fluid), and a central portion between the inlet portion and the outlet portion, wherein the central portion comprises a pumping channel. As used herein, the term "pumping channel" refers to a channel or conduit within the region of compression (as defined earlier) in which a fluid is moved from one end to another end by a peristaltic motion. The peristaltic motion of a fluid is induced by engaging an actuator with the deformable portion of the substrate layer or the load concentrator such that the deformable portion of the substrate layer within the region of compression can deform, thus changing the volume of the underlying fluidic conduit(s), thereby controlling the volume of a fluid flowing through the fluidic conduit(s).

Figure 8:
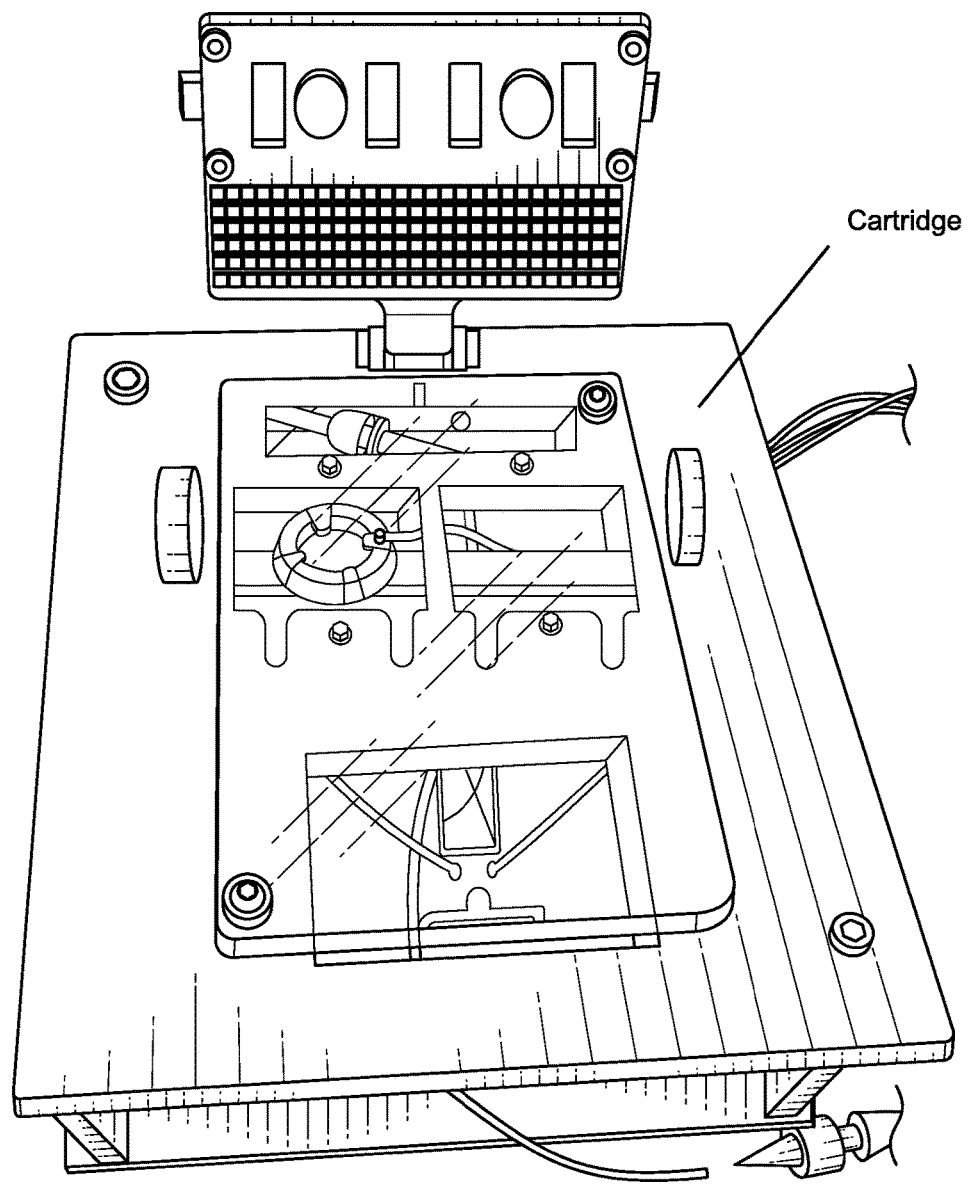
FIG. 8 is a photograph showing use of one embodiment of a fluid-flow control device described herein in a microfluidic application. The fluidic components of the fluid-flow control device are housed on a cartridge that can also hold a microfluidic device, e.g., an organ-on-a-chip.

In some embodiments where there are more than one fluidic conduits in the fluid-flow control device described herein, while each of the fluidic conduits can have their own individual inlets and outlets, at least some fluidic conduits can share the same inlets and outlets. In some embodiments, a fluidic conduit can be a stand-alone fluidic conduit 103, e.g. as shown in FIG. 1. In other embodiments where a fluid-flow control device is integrated directly into a system or an element of the system, a fluidic conduit can be a continuation of a fluidic conduit from/to another device or system, e.g., as shown in FIG. 8. For example, the inlet portion of the fluidic conduit can be adaptably connected to a fluid reservoir or another device or system, which supplies a fluid, while the outlet portion of the fluidic conduit can be adaptably connected to a device or system, e.g., an organ-on-chip device, thus directing a fluid flowing into the device or system. For example, examples of an organ-on-chip-devices that are applicable for use with the fluid-flow control devices described herein include, but are not limited to, the ones described in U.S. Provisional Application No. 61/470,987, filed Apr. 1, 2011; Ser. No. 61/492,609, filed Jun. 2, 2011; Ser. No. 61/447,540, filed Feb. 28, 2011; Ser. No. 61/449,925, filed Mar. 7, 2011; No. 61/697,121, filed on Sep. 5, 2012, and No. 61/569,029, filed on Dec. 9, 2011, in U.S. patent application Ser. No. 13/054,095, filed Jul. 16, 2008 (which discloses, e.g., that various types of cells may be implanted on the surfaces of a membrane of an organ-on-a-chip), and in International Application No. PCT/US2009/050830, filed Jul. 16, 2009, No. PCT/US2012/068766 filed Dec. 10, 2012, No. PCT/US2012/068787 filed Dec. 10, 2012, and No. PCT/US2010/021195, filed Jan. 15, 2010, the contents of each application are incorporated herein by reference.

Figure 6:
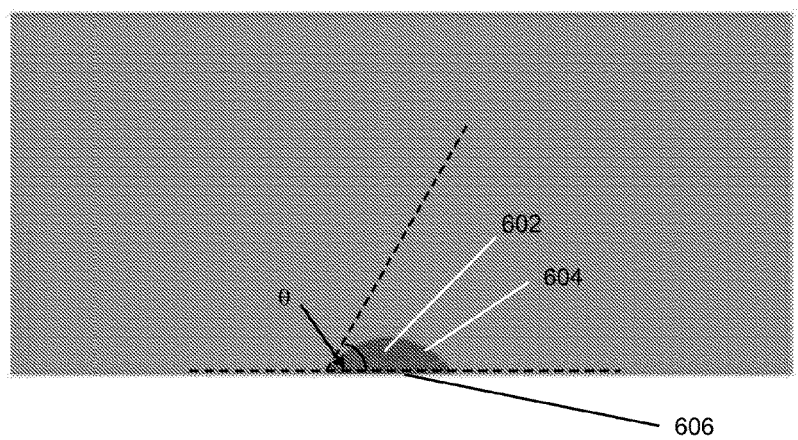
FIG. 6 is a schematic representation showing a cross-sectional view of a semi-circular channel defined in a deformable portion of a substrate layer, e.g., an elastomeric layer or membrane.

The fluidic conduit(s) can have a cross-section of any shape, e.g., rectangular, square, circle, semi-circle, oval, polygon, irregular-shaped, or any combinations thereof. In some embodiments, the cross-sectional shape of the fluidic conduit(s) can be selected to reduce the compression force needed to effect pumping and/or valving, e.g., to reduce leakage of a fluid. For example, in some embodiments, at least one of the fluidic conduits 602 can have a rounded cross-section, e.g., a semi-circular cross-section, as shown in FIG. 6. Without wishing to be bound by theory, rounded fluidic conduits generally require less force to pinch off and thus reduce sensitivity to compression-force variation. Hence, such cross-sections can reduce leakage of a fluid, and is less likely to tear during use than when rectangular corners are present. In some embodiments, at least one of the fluidic conduits 602 can comprise at least one surface 604 at a contact angle θ of about 50 degrees to about 70 degrees relative to another surface that defines a boundary 606 of the fluidic conduit. In one embodiment, at least one of the fluidic conduits 602 can comprise at least one surface 604 at a contact angle of about 60 degrees relative to another surface that defines a boundary 606 of the fluidic conduit, which can further reduce the compression force and leakage of the system.

The fluidic conduits(s) can be defined and arranged in the substrate layer and/or solid body in any pattern, e.g., linear, circular, partially circular 103 (FIG. 1), spiral, rectangular, polygonal, irregular-shaped, concentric, or any combinations thereof. In some embodiments, the fluidic conduit(s) can be each independently of the same or different length.

In some embodiments, the fluid-flow control devices described herein can comprise multiple fluidic conduits disposed in the deformable portion of the substrate layer. In these embodiments, each fluidic conduit can comprise an inlet portion, an outlet portion, and a central portion between the inlet portion and the outlet portion, wherein the central portion comprises a pumping channel. In some embodiments, the inlet portion of each fluidic conduit can be connected to the same inlet port or a different inlet port. In some embodiments, the outlet portion of each fluidic conduit can be connected to the same outlet port or a different outlet port. In some embodiments, having the inlet portion of each fluidic conduit connected to the same inlet port and each outlet portion connected to the same outlet port can be used to increase flow rate and/or protect against channel blockage. In alternative embodiments, having the inlet portion of each fluidic conduit connected to a different inlet port and each outlet portion connected to a different outlet port can be used to pump several different fluids simultaneously and without crosstalk.

In some embodiments, the pumping channels of the multiple fluidic conduits can be arranged in a pattern of a concentric circle.

In some embodiments, the pumping channels of the multiple fluidic conduits can be arranged in an array of linear channels.

In various aspects, the fluid-flow control devices described herein can be configured for fluidic conduits of different sizes, depending on types and/or nature of applications (e.g., microfluidic or low-volume fluid flow applications vs. non-microfluidic or high-volume fluid flow applications). Without wishing to be bound by theory, larger fluidic conduits of the devices described herein can be generally used for higher desirable volume of fluid flow or fluid to be transferred, and smaller fluidic conduits for lower desirable volume of fluid flow or fluid to be transferred. In some embodiments, the fluid-flow control devices are configured for microfluidic applications, e.g., for fluid transfer and/or delivery in a microfluidic platform such as a microfluidic device. Accordingly, in some embodiments, at least one of the fluidic conduits configured to be in contact with the deformable portion of the substrate layer can comprise a microfluidic channel.

As shown in FIGS. 3A-3D, in some embodiments of various aspects described herein, the substrate layer 300 of the fluid-flow control devices can be placed or affixed to a solid body 304. The solid body can be rigid or deformable.

Figure 3A:
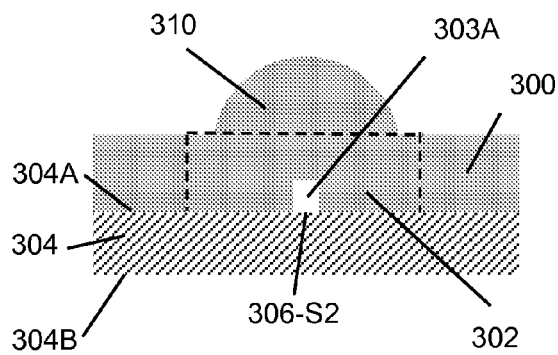
FIGS. 3A-3D are schematic representations showing cross-sectional views of various embodiments of fluid-flow control devices being placed on a solid body.

In some embodiments of various aspects described herein, one or more fluidic conduits can be defined in a separate solid (e.g., non-deformable or less deformable) body and/or in the substrate layer. In some embodiments, as shown in FIG. 3C, at least a portion of the central portion of the fluidic conduit(s) 303C can be defined in a top surface 304A of the solid body 304, while a portion of the bottom surface 302B of the deformable portion 302 can define the top boundary 306-S1 of the fluidic conduit(s) 303C. In some embodiments, the solid body 304 can be non-deformable or less deformable than the deformable portion 302.

In some embodiments, to provide more precise alignment of the pumping channel of one or more fluidic conduits with mechanical components (e.g., the rolling elements disposed in the actuator), at least a portion of the pumping channel can be defined in the deformable portion 302. Referring to FIG. 3A, in some embodiments, at least a portion of the pumping channel of the one or more fluidic conduits can be defined in the bottom surface 302B of the deformable portion 302, while a portion of the top surface 304A of the solid body 304 can define the bottom boundary 306-S2 of the pumping channel 303A. In these embodiments, the fluid conduits 303A and the deformable portion 302 of the substrate layer can be manufactured together, so that they are generally well aligned with each other. Additionally or alternatively, as shown in FIG. 3D, at least a portion of the pumping channel 303D can be defined between the top 302A and bottom 302B surfaces of the deformable portion.

Figure 3B:
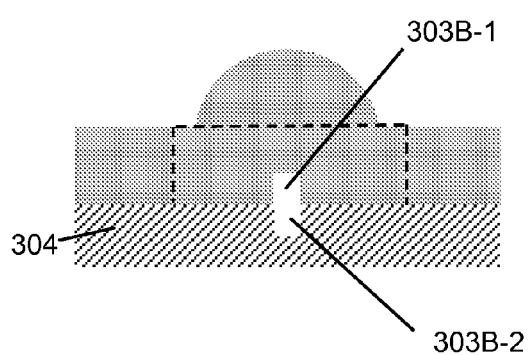
Figure 3C:
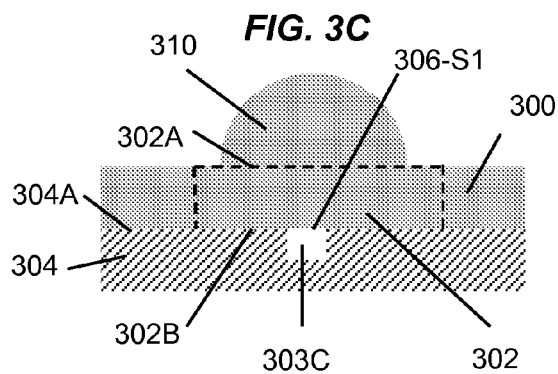
Figure 3D:
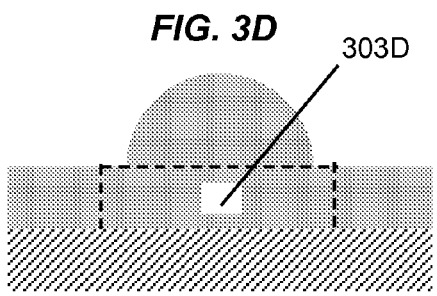

In some embodiments, as shown in FIG. 3B, a first sub-channel 303-B1 can be defined in the bottom surface 302B of the deformable portion 302 and a second sub-channel 303B-2 can be defined in the top surface 304A of a solid body 304. In these embodiments, a fluidic conduit can be formed by aligning the first sub-channel with the second sub-channel such that the first sub-channel provides a top boundary of the resultant fluidic conduit and the second sub-channel provides a bottom boundary of the resultant fluidic conduit.

Roll-Off Portion (Feature (ii) of Table 1):

In some embodiments, the fluid-flow control device can comprise one or more roll-off portions that enable the pressure applying elements (e.g., actuator rollers) to gradually engage or disengage by applying a gradual change in pressure on the central portion of the fluidic conduits.

Figure 10A:
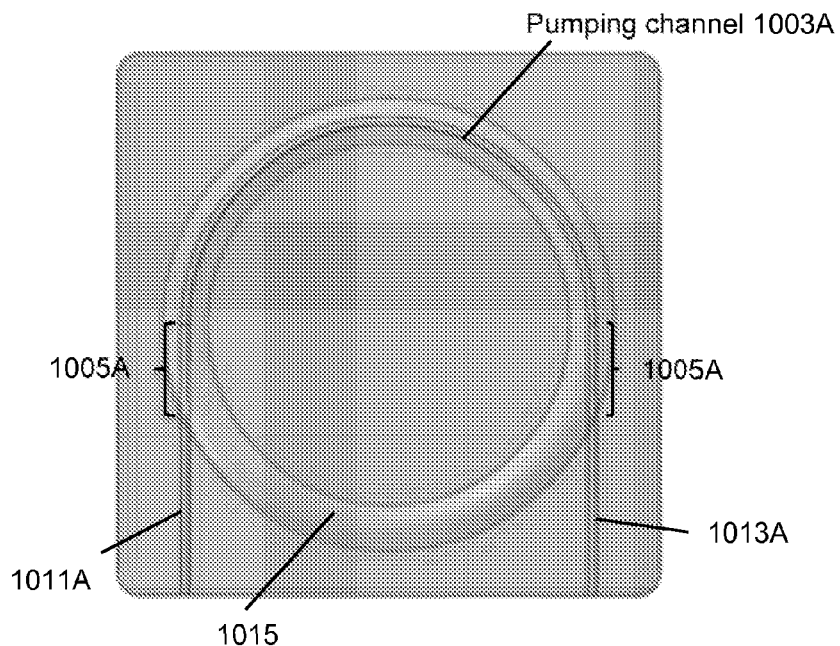
FIGS. 10A-10B are transparent top views of fluid-flow control devices according to some embodiments described herein, showing an underlying microfluidic channel, wherein the microfluidic channel comprises a pumping channel (PC) and a roll-off portion (ROP).
Figure 10B:
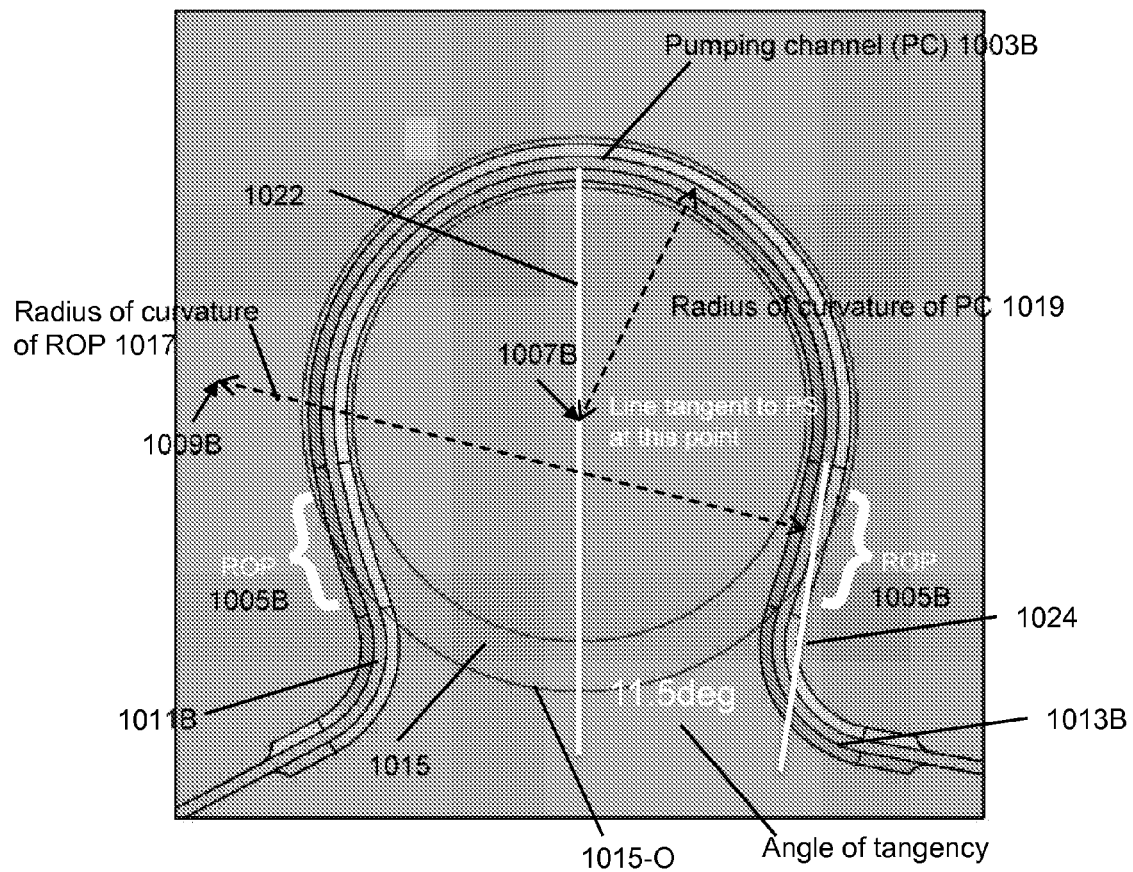

Referring to FIGS. 10A-10B, the fluid-flow control device comprises a fluidic conduit disposed in the deformable portion of a substrate layer. The fluidic conduit comprises an inlet portion 1011A, 1011B, an outlet portion 1013A, 1013B and a central portion between the inlet portion and the outlet portion, and wherein the central portion comprises a pumping channel 1003A, 1003B. The fluid-flow control device further includes a region of compression 1015 which defines the area which is contacted by the force applying elements (e.g., actuator rollers) that compress the deformable portion of the substrate layer and the fluidic conduit.

In some embodiments, the roll-off portion 1005A, 1005B can be located between the pumping channel 1003A, 1003B and the inlet portion 1011A, 1011B, where the fluidic conduit extends outside of the region of compression 1015. In some embodiments, the roll-off portion 1005A, 1005B can be located between the pumping channel 1003A, 1003B and the outlet portion 1013A, 10113B, where the fluidic conduit extends outside of the region of compression 1015. In some embodiments, a fluidic conduit can comprise a first roll-off portion 1005A, 1005B between the inlet portion 1011A, 1011B and the pumping channel 1003A, 1003B and a second roll-off portion 1005A, 1005B between the outlet portion 1013A, 10113B and the pumping channel 1003A, 1003B.

In some embodiments, as shown in FIG. 10A, the roll-off portion 1005A includes an effective radius of curvature of infinity, i.e., a straight channel. In this embodiment, there can be considerable pulsatility when the roll-off portion is linear. Without wishing to be bound by theory, pulsatile flow downstream of a fluid-flow control device can be generated as the pump-head roller disengages (or engages) the pumping channel, and thus creates a rapid volume change in the flow path.

One of the solutions to mitigating this source of pulsatile flow is to design the path of roll-off portion to gradually extend outside of a region of compression 1015 such that during operation, rolling elements can be gradually disengaged from (or engaged with) the corresponding fluid conduit, thereby mitigating pulsatile flow that would be generated otherwise. Once the roll-off portion is outside the region of compression 1015, the rest of the fluid conduit (e.g., the outlet portion or inlet portion) can be routed in any manner (as the fluid conduit outside the region of compression is not significantly affected by the pump behavior). Accordingly, the term "roll-off portion" refers to a channel extending within the region of compression 1015 that couple the pumping channel to the inlet portion or outlet portion, wherein the path of the channel is designed to allow rolling elements to disengage from (or to engage with) the channel in a gradual manner. Thus, the length of the roll-off portion depends on the dimensions of the region of compression and the path and/or curvature of the roll-off portion.

The term "region of compression" as used herein refers to a region in which a stress field or a strain field would generate around a channel in the underlying deformable portion due to an applied compressive force or pressure (e.g., by a rolling element such as roller of an actuator) at a given time during operation of the fluid-flow control devices described herein. The applied compressive force or pressure to generate the region of compression 1015 is sufficient to compress between 10% and 100% (including 10% and 100%) of the pumping channel volume. In some embodiments, the applied compressive force or pressure can be sufficient to compress at least about 50% of the pumping channel volume or more, including, e.g., at least about 60%, at least about 70%, at least about 80%, at least about 90% or more, of the pumping channel volume. In one embodiment, the applied compressive force or pressure can be sufficient to compress 100% of the pumping channel volume For example, FIGS. 10A-10B show a circular region of compression 1015 that a roller generates. The region of compression 1015 can be determined by computationally modeling application of applying a given force to a deformable portion based on the design and configuration of the fluid flow-control device, including, e.g., but not limited to, properties of a load concentrator (e.g., size, shape, material properties), dimensions and/or shape of the pumping channel, applied force, dimensions and/or shape of a rolling element to be engageable with the deformable portion or the load concentrator, material properties of the deformable portion, thickness of the substrate material between the pumping channel to be compressed and compression surface, and any combinations thereof. A stress or strain field in the deformable region can then be mathematically determined to estimate a region of compression. In some embodiments, the region of compression 1015 can be characterized by the width of compression area. Additionally, the region of compression can be determined or approximated experimentally using a suitable test structure, wherein the roller's effect on an underlying channel is observed.

In some embodiments where the deformable portion includes a load concentrator, the region of compression 1015 can be an area wider than the dimension of the contact surface of the load concentrator, as there can be radial force transmission within the deformable portion of the substrate layer. In some embodiments where ball bearings are used as rolling elements to deform the deformable portion, the region of compression 1015 can have a finite width.

In some embodiments, the roll-off portion 1005B includes a positive radius of curvature or a positive effective radius of curvature with respect to the curvature of the preceding or following portion of the pumping channel, which depends on the location of the roll-off portion. Such roll-off portion can help reduce rapid pressure changes that can accompany peristaltic action in the pump-head and thus reduce pulsatile flow.

As used herein, the term "effective radius of curvature" refers to a radius of curvature when the roll-off portion or the pumping channel forms a circular arc or a combination of radii of curvature when the roll-off portion or the pumping channel does not form a circular arc. For example, for a curved line, the radius of curvature at a given point along the curved line is the radius of a circle that mathematically best fits the curve at that point. Thus, a non-circular arc includes radii of curvatures determined at various points along the arc.

Generally, the radii of curvatures can be generally measured from the centerline, inner boundary, or outer boundary of a channel. Accordingly, with respect to the roll-off portion, the radii of curvatures can be generally measured from the centerline, inner boundary or outer boundary of the channel defined within the roll-off portion.

As used herein, the term "positive effective radius of curvature" refers to the roll-off portion curving inwardly with respect to the curvature of the preceding or following portion of the pumping channel, which depends on the location of the roll-off portion. Stated another way, the roll-off portion has a positive effective radius of curvature when the roll-off portion forms a concave arc (i.e., toward the inside of the pump channel) with respect to the curvature of the preceding or following portion of the pumping channel, which depends on the location of the roll-off portion.

For illustration purposes only, as shown in FIG. 10B, when the pumping channel 1003B forms a circular arc with a center of curvature 1007B, the roll-off portion 1005B having a positive effective radius of curvature indicates that the center of curvature 1009B that is used to determine the effective radius of curvature of the roll-off portion 1005B is toward the inside of the pumping channel 1003B where its center 1007B is located. In contrast, if the roll-off portion 1005B has a negative effective radius of curvature, it indicates that the center of curvature 1009B of the roll-off portion 1005B is on the outside of the pumping channel 1003B that is opposite to the side where the center 1007B is located. That is, a negative effective radius of curvature would yield a roll-off portion with a convex arc (i.e., toward the inside of the pump channel) with respect to the preceding or following portion of the pumping channel.

In accordance with some embodiments of the invention, the roll-off portion can generally have a positive radius or a positive effective radius of curvature of any value, excluding infinity (e.g., a straight path). The curvature of the roll-off portion can depend on, for example, the overall size of the pump (e.g., radius of the pump channel), and/or the location of the inlet and outlet relative the region of compression. In some embodiments where the inlet portion 1011B and outlet portion 1013B are placed outside the outer boundary 1015-O of the region of compression 1015 of the pumping channel, the effective radius of curvature of the roll-off portion 1017 can be larger than the radius of curvature of the pumping channel 1019. In these embodiments, the roll-off portion can spiral out of the region of compression. For example, the effective radius of curvature of the roll-off portion can be larger than the radius of curvature of the pumping channel by at least about 10% or more, including, e.g., at least about 20%, at least about 30%, at least about 40%, at least about 50%, at least about 60%, at least about 70%, at least about 80%, at least about 90%, at least about 95% or more. In some embodiments, the effective radius of curvature of the roll-off portion can be larger than the radius of curvature of the pumping channel by at least about 1.5-fold or more, including, e.g., at least about 2-fold, at least about 3-fold, at least about 4-fold, at least about 5-fold, at least about 6-fold, or more. In some embodiments, the effective radius of curvature of the roll-off portion can be at least 4 times or more, larger than the radius of curvature of the pumping channel.

In one embodiment where the pumping channel forms a circular conduit with a radius of curvature of 5 mm, the roll-off portion can have a positive radius of curvature of about 15 mm to about 30 mm. In one embodiment, the roll-off portion can have a positive radius of curvature of about 20 mm.

In some embodiments where at least one of the inlet portion 1011B and outlet portion 1013B are circumscribed by the outer boundary 1015-O of the region of compression 1015 of the pumping channel, the effective radius of curvature of the roll-off portion can be smaller than the radius of curvature of the pumping channel. For example, the effective radius of curvature of the roll-off portion can be no less than 25% of the radius of the pumping channel, including, e.g., no less than 30%, no less than 35%, no less than 40%, no less than 45%, no less than 50%, no less than 55%, no less than 60%, no less than 65%, no less than 70%, no less than 75%, no less than 80%, no less than 85%, no less than 90%, no less than 95%, of the radius of the pumping channel.

In some embodiments, the roll-off portion does not have a negative effective radius of curvature.

In some embodiments, the roll-off portion does not comprise a sharp turn, i.e., with a pointed angle.

The angle of tangency of the location where the pumping channel ends and the roll-off portion begins can vary with a number of factors, including, e.g., but not limited to, pumping channel size, pump size and speed, routing direction of the fluidic conduit before and/or after the pumping channel, or any combinations thereof. The phrase "angle of tangency of the roll-off portion" refers to the angle formed by a tangent line 1024 to the pumping channel at the point where the pumping channel ends and roll-off portion begins and the central axis of the pumping channel 1022. In some embodiments, the angle of tangency between the pumping channel and the roll-off portion can vary from about 1 degree to about 45 degrees, or from about 5 degrees to about 30 degrees, or from about 10 degrees to about 20 degrees. The angle of tangency of 11.5 degrees shown in FIG. 10B is an illustrative example and is not intended to be limiting.

The roll-off portion can have a channel height that is the same as or different from that of the preceding or following portion of the pumping channel. In some embodiments, the roll-off portion can initially have the same channel height as the preceding or following portion of the pumping channel around the junction, and subsequently adopt a different height. The roll-off portion can have a uniform or varying channel height across the length of the roll-off portion. The channel height can change over the extent of the roll-off portion to further mitigate pulsatile flow.

The roll-off portion can have a channel width same as or different from that of the preceding or following portion of the pumping channel. In some embodiments, the roll-off portion can initially have the same channel width as the preceding or following portion of the pumping channel around the junction, and subsequently adopt a different width. The roll-off portion can have a uniform or varying channel width across the length of the roll-off portion. The channel width can change over the extent of the roll-off portion to further mitigate pulsatile flow.

Load Concentrator (Feature (i) of Table 1)

Referring to FIGS. 1-3D, in some embodiments, the fluid-flow control device described herein can comprise the feature (i), i.e., the deformable portion 102, 202, 302 including at least one load concentrator 110, 210A-C, 310. As used herein, the term "load concentrator" refers to a structural element designed to direct and/or focus a force applied thereon to at least a portion of the deformable portion comprising a fluid conduit disposed therein. Thus, the load concentrator can better direct a force applied by the actuator to the deformable portion and alleviate the alignment demands between the mechanical components and the deformable portion as required in the existing micropumps.

Accordingly, in another aspect, provided herein is a fluid-flow control device comprising (a) a substrate layer comprising a deformable portion, the deformable portion including at least one load concentrator; and (b) one or more fluidic conduits disposed in the deformable portion, wherein at least one of the fluidic conduits comprises: an inlet portion for receiving a fluid, an outlet portion for outputting the fluid, and a central portion between the inlet portion and the outlet portion, and wherein the central portion comprises a pumping channel, the pumping channel being aligned with said at least one load concentrator.

In some embodiments, the fluid-flow control device can further comprise an actuator configured to be engageable with the load concentrator to deform the deformable portion and pumping channel such that the fluid is forced to move through the central portion from the inlet to the outlet as the actuator applies a pressure to the load concentrator.

Figure 9A:
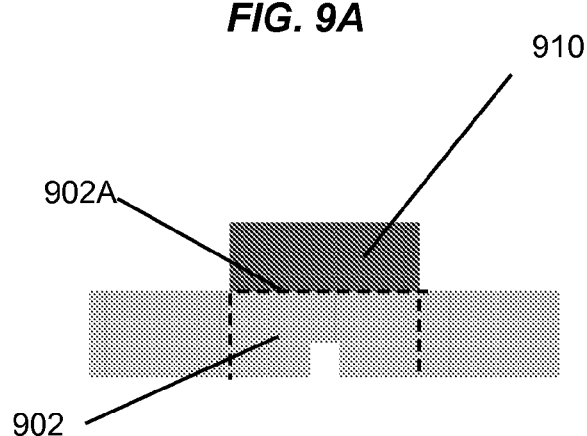
FIGS. 9A-9C are diagrammatic cross-sectional views of fluid-flow control devices having a load concentrator according to some embodiments described herein.
Figure 9B:
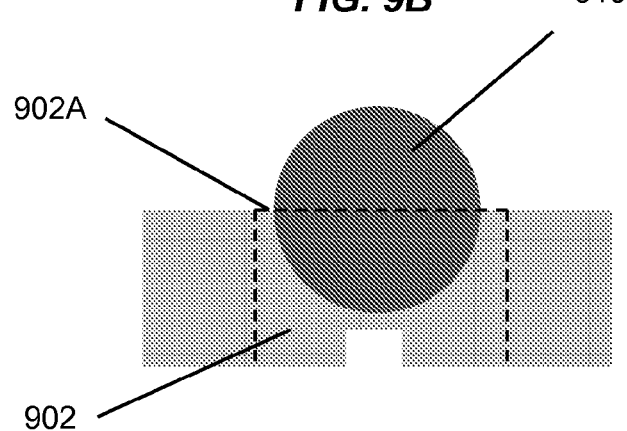
Figure 9C:
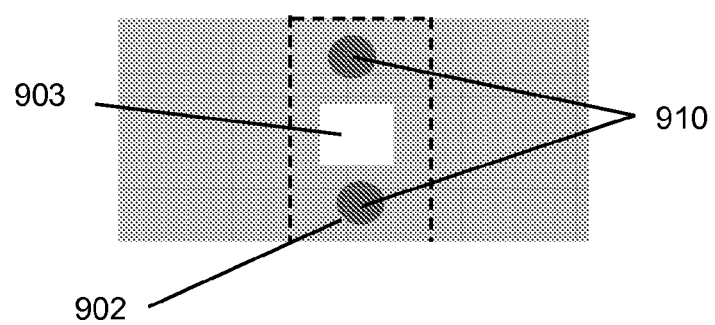

One or more load concentrators can be placed in any configuration in the deformable portion. For example, in some embodiments as shown in FIG. 9A, at least one load concentrator 910 can be formed on the top surface 902A of the deformable portion 902. In some embodiments as shown in FIG. 9B, at least a portion of the load concentrator 910 can be embedded below the top surface 902A of the deformable portion 902. In some embodiments, as shown in FIG. 9C, at least one load concentrator 910 can be embedded inside the deformable portion 902, wherein the load concentrator 910 can be placed above and/or below the fluidic conduit 903. In some embodiments where at least part of the load concentrator embedded inside the deformable portion, a portion of the load concentrator surface can be in contact with or above the boundary of the fluidic conduit. While the load concentrators shown in FIGS. 9A-9C each have a defined shape, it is not intended to be limiting and a load concentrator having any shape can be used.

In general, the load concentrator can have a cross-section in any shape, e.g., but not limited to, a circle, a semi-circle, an oval, a rectangle, a square, a polygon, a triangle, an irregular shape, or any combinations thereof. In some embodiments, the load concentrator is a ring.

In some embodiments, the portion of the load concentrator that is engageably in contact with an actuator or a rolling element can have a surface contour conforming to the shape of the contact portion of the actuator or the rolling element.

In some embodiments, the load concentrator can comprise a protruding surface. As used herein, the term "protruding surface" generally refers to a load concentrator having an outwardly extending surface that extends in to a top surface of the deformable portion. Stated another way, a "protruding surface" can refer to at least a portion (e.g., at least about 50%, at least about 60%, at least about 70%, at least about 80%, at least about 90% or more) of a surface projecting or bulging outward. A protruding surface can be angled or curved. For example, in some embodiments of FIGS. 1-2C, the protruding surface can form or have a cross-section of a circle, a semi-circle 112, an oval, a square, a rectangle 210A, a polygon 210B, an irregular shape 210C or any combinations thereof.

In some embodiments, the load concentrator 110 can be a structurally solid element comprising a rounded convex surface, e.g., a bump, as shown in FIG. 1 or FIG. 9B. In some embodiments, the load concentrator 110 can be a structurally solid element comprising a rectangular protruding surface.

In some embodiments, the load concentrator can be formed of a material substantially same as that of the deformable portion.

In some embodiments, the load concentrator can be formed of a material different from that of the deformable portion. For example, the material forming the load concentrator can be less deformable than the material forming the deformable portion. The less deformable material is generally more efficient than a more deformable material in transferring localized deflection or deformation through the material. Thus, by using a less deformable material for engaging with a pumphead, the amount of deflection or deformation of the load concentrator required to create a pumping action in the fluid-flow control device can be reduced, thus reducing overall compressive force to create peristalsis of a fluid through the fluid conduit.

In addition, by using different materials in the load concentrator and the deformable portion, one can choose a material optimized for its individual property requirements. For example, one can choose a material for a load concentrator based on the mechanical compatibility and durability (e.g., to minimize wear due to friction under rollers), while choosing a different material for the deformable portion based on the bio- or solvent-compatibility.

The phrase "less deformable than the material forming the deformable portion" as used herein refers to a material in which the amount of deformation or deflection is less than that of the material forming the deformable portion, when both materials are subjected to substantially the same level of pressure. For example, when the less deformable material is subjected to a given pressure, the amount of deformation or deflection in the less deformable material can be between 1% and 95% of the amount of deformation or deflection that would be observed in a material forming the deformable portion when it were to be subjected to the same given pressure. In accordance with some embodiments of the invention, when subject to the same pressure, the less deformable material will deform about 10%, about 15%, about 20%, about 25%, about 30%, about 35%, about 40%, about 45%, about 50%, about 55%, about 60%, or more of the more deformable material. In accordance with some embodiments of the invention, the less deformable material (e.g., the load concentrator) will have an elastic modulus that is about 1.5 times, about 2.0 times, about 2.5 times, about 3.0 time, about 3.5 times or more the elastic modulus of the more deformable material (e.g., the channel or the deformable portion adjacent the channel). In accordance with some embodiments of the invention, when subject to the same pressure, the less deformable material will deform in the range of approximately 10% to 25% of the deformation of the more deformable material.

In some embodiments, the less deformable material selected to form a load concentrator can have a hardness (e.g., based on Shore A scale or Shore D scale) larger than that of a material selected to form the deformable portion of the substrate layer. For example, the hardness of the less deformable material can be higher than that of the material for fabricating the deformable portion by at least about 5% or more, including, e.g., at least about 10%, at least about 20%, at least about 30%, at least about 40%, at least about 50%, at least about 60%, at least about 70%, at least about 80%, at least about 90% or more. In some embodiments, the hardness of the less deformable material can be higher than that of the material for fabricating the deformable portion by at least about 1.1-fold or more, including, e.g., at least about 1.2-fold, at least about 1.5-fold, at least about 2-fold, at least about 3-fold, at least about 4-fold, at least about 25-fold or more. In some embodiments, the hardness of the less deformable material can be higher than that of the material for fabricating the deformable portion by no more than 75% or less, including, e.g., no more than 70%, no more than 60%, no more than 50%, no more than 40%, no more than 30%, no more than 20%, or lower. In accordance with some embodiments of the invention, the hardness of the less deformable material can be in the range of approximately 25% to 35% higher than the material of the deformable portion.

In some embodiments, the less deformable material for a load concentrator can have a hardness value (based on a Shore A scale) of about 35 to about 100, or about 40 to about 90, or about 50 to about 90, or about 60 to about 90, or about 90, or about 50 to about 80, or about 60 to about 80. In some embodiments, the less deformable material for a load concentrator can have a hardness value (based on a Shore A scale) of at least about 50, at least about 60, at least about 70, at least about 80, at least about 90, at least about 95 or higher. In some embodiments, the less deformable material for a load concentrator can have a hardness value (based on a Shore A scale) of about 60 about 80. In some embodiments, the less deformable material for a load concentrator can have a hardness value (based on a Shore A scale) of about 70.

In some embodiments, the less deformable material selected to form a load concentrator can have an elastic modulus or Young's modulus greater than that of a material forming the deformable portion of the substrate layer. For example, the elastic modulus or Young's modulus of the less deformable material can be greater than that of the material for fabricating the deformable portion by at least about 5% or more, including, e.g., at least about 10%, at least about 20%, at least about 30%, at least about 40%, at least about 50%, at least about 60%, at least about 70%, at least about 80%, at least about 90% or more. In some embodiments, the elastic modulus or Young's modulus of the less deformable material can be higher than that of the material for fabricating the deformable portion by at least about 1.1-fold or more, including, e.g., at least about 1.2-fold, at least about 1.5-fold, at least about 2-fold, at least about 3-fold, at least about 4-fold, at least about 5-fold at least about 10-fold, at least about 20-fold, at least about 30-fold, at least about 40-fold, at least about 50-fold, at least about 60-fold, or more. In some embodiments, the elastic modulus of the less deformable material can be 40 to 60 times the elastic modulus of the more deformable material. In some embodiments, the elastic modulus of a component can also be dependent on the geometry or features of the component and any associated components (e.g., adhesives, clamps and fasteners) In some embodiments, the elastic modulus or Young's modulus of the less deformable material can be higher than that of the material for fabricating the deformable portion by no more than 75% or less, including, e.g., no more than 70%, no more than 60%, no more than 50%, no more than 40%, no more than 30%, or lower.

In some embodiments, the less deformable material can have an elastic modulus or Young's modulus of about 0.1 MPa to about 20 MPa, about 1.5 MPa to about 20 MPa, about 2 MPa to about 20 MPa, about 5 MPa to about 20 MPa, or about 10 MPa to about 200 MPa.

An exemplary less deformable material for fabrication of a load concentrator can be silicone rubber, polydimethylsiloxane (PDMS), polyurethane, rubber, gels, hydrogels, molded plastic, polymethylmethacrylate (PMMA), polycarbonate, polytetrafluoroethylene (e.g., TEFLON™), polyvinylchloride (PVC), polysulfone, mixture of hydrocarbon oils, polymers containing plasticizers, synthetic polyisoprene, polybutadiene, chloroprene rubber, polychloroprene, neoprene, baypren, natural rubber, butyl rubber (e.g., copolymer of isobutylene and isoprene), halogenated butyl rubbers (e.g., chloro butyl rubber; bromo butyl rubber), styrene-butadiene rubber (copolymer of styrene and butadiene), styrene-ethylene/butadiene-styrene (SEBS), nitrile rubber (copolymer of butadiene and acrylonitrile), hydrogenated nitrile rubbers, ethylene propylene rubber, ethylene propylene diene monomer (EPDM) rubber, epichlorohydrin rubber, polyacrylic rubber, silicone rubber, fluorosilicone rubber, fluoroelastomers (e.g., VITON™), perfluoroelastomers, polyether block amides, chlorosulfonated polyethylene (e.g., HYPALON™), ethylene-vinyl acetate, thermoplastic elastomers (TPE) (e.g., SANTOPRENE™) and any combinations thereof.

The load concentrator and the deformable portion (of the substrate layer) can be fabricated separately as individual components for subsequent bonding or assembly, or be fabricated as an integral piece. In some embodiments, the load concentrator and the deformable portion of the substrate layer can be fabricated separately and held in position by other components or forces. In some embodiments, the load concentrator and the deformable portion (of the substrate layer) can be fabricated as individual components and then bonded by any method that ensures no relative motion between the two components. Examples of bonding methods include, but are not limited to, acrylate adhesives, two part epoxies, silicone, adhesive, heat staking, thermal boding, solvent and solvent-assisted bonding, laser welding, ultrasonic welding and any combinations thereof. In some embodiments, the load concentrator and the deformable portion (of the substrate layer) can be fabricated as an integral piece by any methods known in the art, e.g., molding such as injection molding, embossing, machining, or 3-D printing. In some embodiments, the load concentrator can be clamped in position by the substrate layer or a separate clamping component. In accordance with some embodiment, the load concentrator can be arranged in position without being clamped or fixed to the substrate layer.

In some embodiments, the load concentrator can be an O-ring. The O-ring should have a higher hardness value than that of the material used in the deformable portion. In these embodiments, since the bottom of the O-ring is generally round, it can apply a force in a more focused manner, similarly to the bearings. However, since the top of the O-ring is also rounded, it can allow use of rolling elements (e.g., flat or cylindrical rollers), which can be loosely aligned to the O-ring and the pumping channel. Accordingly, in one embodiment, the fluid-flow control device can comprise a substrate comprising a deformable portion, wherein the deformable portion includes an O-ring, which has a hardness value or tensile strength greater than that of the material used in the deformable portion. The O-ring can be disposed on a top surface of the deformable portion or molded into the deformable portion.

In some embodiments where substrate layer comprises more than one deformable portions (e.g., 2 or more deformable portions), each of the deformable portions can independently include at least one load concentrator or none. Accordingly, in some embodiments, at least two or more deformable portions can each include a load concentrator.

Dimensions of the load concentrators can vary with dimensions of the fluidic conduits configured to be in contact with the deformable portion. In general, a larger deformable portion of the substrate layer and thus a larger load concentrator is desired to accommodate a larger fluidic conduit. Accordingly, the dimensions of the load concentrator can range from microns to centimeters, e.g., depending on types of applications (e.g., microfluidic vs. non-microfluidic applications). For example, in some embodiments, the height (or thickness) of the load concentrator can range from about 10 µm to about 30 mm, or from about 20 µm to about 20 mm, or from about 30 µm to about 10 mm. In one embodiment, the height (or thickness) of the load concentrator can be about 1 mm. In some embodiments, e.g., for microfluidic applications, the height (or thickness) of the load concentrator can range from about 10 µm to about 1000 µm, or from about 20 µm to about 900 µm, or from about 30 µm to about 800 µm, or from about 40 µm to about 700 µm, or from about 50 µm to about 600 µm, or from about 100 µm to about 500 µm. In some embodiments, e.g., for non-microfluidic applications, the height (or thickness) of the load concentrator can range from about 1 mm to about 50 mm, or from about 5 mm to about 40 mm, or from about 10 mm to about 30 mm.

In some embodiments where a less deformable material is selected for the load concentrator, the thickness of the load concentrator can be determined by the amount of deflection/deformation is needed to collapse an underlying pumping channel and the overall size of the fluid-flow control device. Without wishing to be bound by theory, due to the increased stiffness/hardness of material used in the load concentrator, the contact points between the actuator and/or rolling elements (e.g., pumphead rollers) and the load concentrator need to be sufficiently spaced in order for the underlying pumping channel to collapse in only the area underneath the actuator and/or rolling elements. If the contact points are too close, the load concentrator can be sufficiently rigid to compress and collapse the entire length of the pumping channel simultaneously. Thus, no fluid can flow as no peristaltic motion is produced.

The fluid-flow control device (e.g., the substrate layer comprising a deformable portion) can be detachable from the actuator or driving element (e.g., a motor). Thus, the fluid-control device can be disposable and replaced, if needed, while the actuator or driving element (e.g., a motor) and other mechanics can be retained. Accordingly, another aspect provided herein is a fluid-flow control device comprising: a substrate layer comprising a deformable portion, the deformable portion including a load concentrator described herein.

In some embodiments of this aspect and other aspects described herein, the fluid-flow control device can further comprise one or more fluidic conduits disposed in the deformable portion, wherein at least one of the fluidic conduits comprises: an inlet portion for receiving a fluid, an outlet portion for outputting the fluid, and a central portion between the inlet portion and the outlet portion, wherein the central portion comprises a pumping channel.

As described above, in some embodiments, one or more fluidic conduits can be defined in a bottom surface of the deformable portion of the substrate layer. Since the fluidic conduits and load concentrator can be manufactured together in these embodiments, they are readily aligned with each other. Accordingly, in some embodiments, a cylindrical rolling element (e.g., a cylindrical roller) can be used to engage the load concentrator to affect pump and/or valve action. Without wishing to be bound by theory, as cylindrical rollers do not generally require precise alignment, these embodiments can effectively eliminate the alignment concern.

In some embodiments of this aspect and other aspects described herein, a top surface of the load concentrator can be further configured to be coupled with one or more rolling elements described herein, thereby forming a "snap-on rolling element" for plug-and-play applications, which is further described in detail later. In some embodiments, the rolling elements can be configured to be engageable with an actuator to deform the deformable portion.

Rolling Elements and/or Low Friction Material (Feature (iv) of Table 1)

In some embodiments of various aspects described herein, the fluid-flow control device can comprise the feature (iv), i.e., the actuator comprising at least one (including, e.g., at least 2, at least 3, at least 4, at least 5, at least 6, at least 7, at least 8, at least 9, at least 10, or more) rolling element and/or at least one (including, e.g., at least 2, at least 3, at least 4, at least 5, at least 6, at least 7, at least 8, at least 9, at least 10, or more) low friction material. In some embodiment, at least one rolling element and/or at least one low friction material can be mechanically connected to a shaft fixed to the actuator or engageable to a driving element (e.g., a motor). In some embodiments, the precise positioning can be done with any motor shaft encoder or servo motor, thus improving the robustness of the valve implementation of this design. Further, such embodiments of the fluid-flow control device can prevent rolling elements (e.g., ball bearings) from slipping with respect to a driving element (e.g., a motor), which is in particular a problem for existing valves.

Any types of art-recognized rolling elements, e.g., to provide a compressive force to deform or compress the pumping channel, can be utilized in the fluid-flow control devices described herein. Examples of rolling elements can include, but are not limited to, ball bearings, plain bearings (e.g., but not limited to, sleeve bearings), roller bearings (e.g., but not limited to, cylindrical rollers, rounded (convex) rollers, needle rollers, tapered rollers, and spherical rollers) or any combinations thereof. The shape of the rolling elements can vary, for example, with the design of the actuator and/or load concentrator. In some embodiments, the rolling elements can be cylindrical, tapered, convex, spherical, irregular-shaped, or any combinations thereof.

Figure 4:
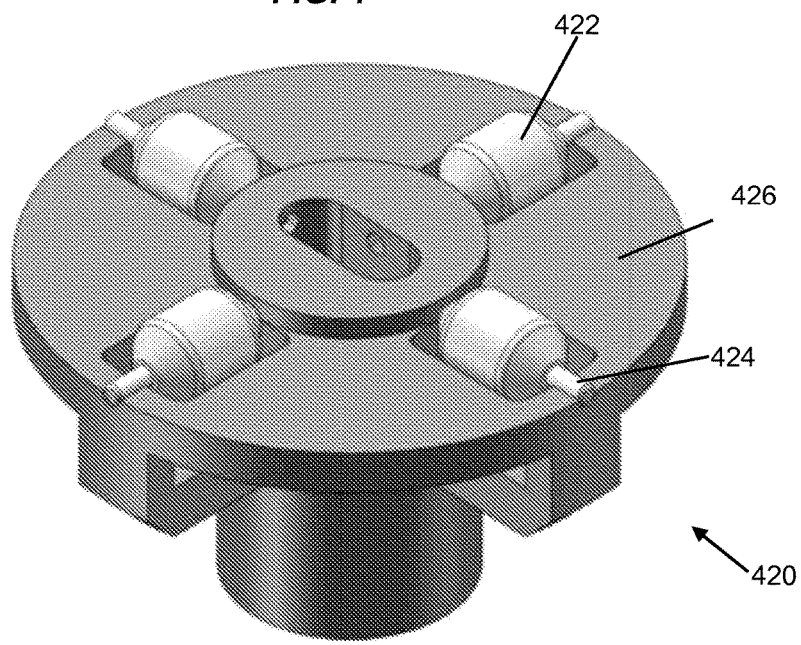
FIG. 4 is a schematic representation of a portion of an actuator comprising a roller assembly, e.g., a roller carriage holding rolling elements (e.g., cylindrical rollers) configured to rotate on a shaft fixed to the roller carriage.

In some embodiments, the actuator can comprise at least one (including, e.g., at least 2, at least 3, at least 4, at least 5, at least 6, at least 7, at least 8, at least 9, at least 10, or more) roller bearings. In some embodiments, as shown in FIG. 4, the actuator 420 can comprise two or more (e.g., 2, 3, 4, 5, 6, 7, 8, 9, 10, or more) roller bearings, e.g., cylindrical rollers 422, that can rotate on bearings or on a shaft 424, e.g., fixed to the actuator 420. In some embodiments, the rollers can be further tapered. In some embodiments, the rollers 422 disposed in a roller carriage 426 can each have variable length and/or placement, which can be desirable in mixing applications. In one embodiment, no ball bearings are utilized in the actuator or fluid-flow control devices described herein.

In some embodiments, the rolling element(s) can comprise at least one rounded contact surface. For example, this can be implemented using an O-ring or a functional equivalent thereof rotating on a rod structure, e.g., a shoulder screw, and/or as a rounded roller, and/or rounded protrusion on the surface of a cylindrical roller.

In some embodiments, the actuator can comprise at least one low friction material capable of sliding against the deformable portion of the substrate layer, e.g., without rolling. In some embodiments, the low fiction material applicable for use to slide against the deformable portion of the substrate layer can have a dynamic coefficient of friction against steel of about 0.1 to about 0.5. Examples of such low friction materials can include, but are not limited to, polytetrafluoroethylene (PTFE), acetal, DELRIN®, RULON®, CELCON®, HOSTAFORM®, and any combinations thereof. The use of a low friction material to slide against the deformable portion without rolling can be amenable to easy and inexpensive manufacture.

Figure 5:
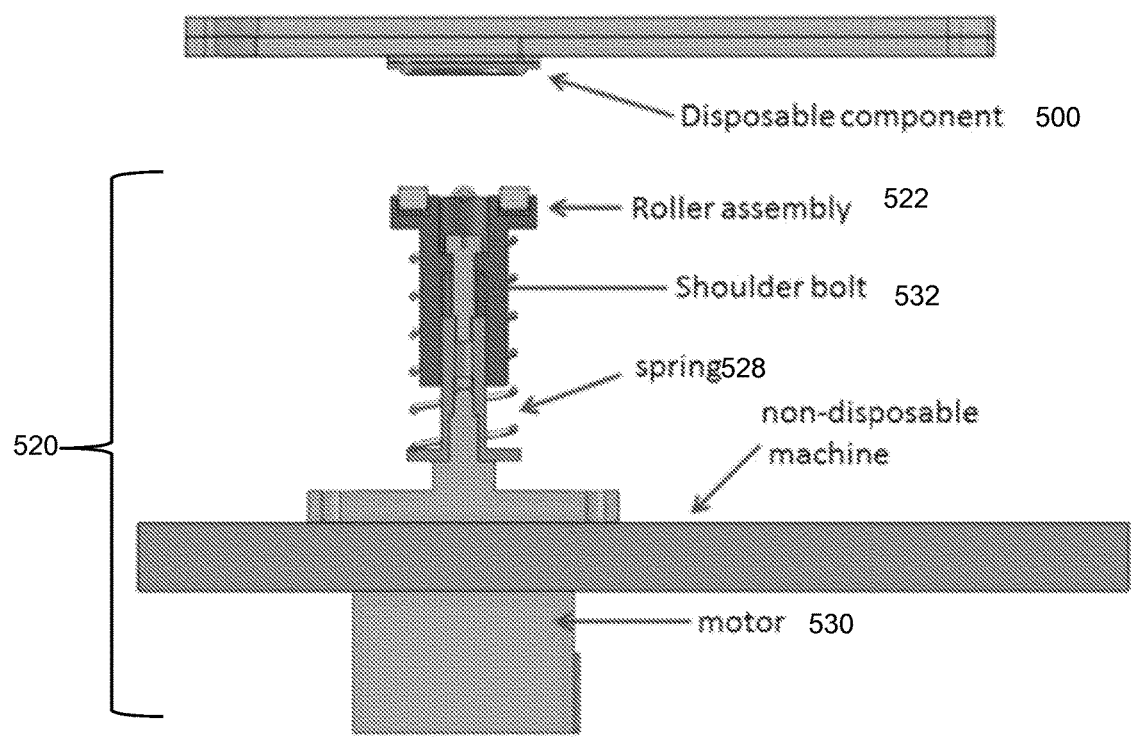
FIG. 5 is a schematic representation of one embodiment of a fluid-flow control device described herein, which comprises two separate components: non-disposable mechanical component and disposable substrate (e.g., elastomeric) manifold. The non-disposable mechanical component includes an actuator comprising a spring mechanically coupled to a roller assembly and a motor to drive or rotate the actuator. The shoulder bolt in the roller assembly pre-loads the spring. The disposable substrate (e.g., elastomeric) manifold is disposed on a solid body (e.g., a disposable cartridge that holds a microfluidic device) to form a channel.

Referring to FIG. 5, in some embodiments of various aspects described herein, the actuator 520 can further comprise a driving element, e.g., a motor, to drive the movement of the rolling elements 522. While FIG. 5 illustrates a set-up appropriate for rotary motion of the rolling elements, the design of the actuator, motor and/or rolling elements can be adapted for linear or any other kinds of motion, e.g., random, or zigzag motions.

Figure 7:
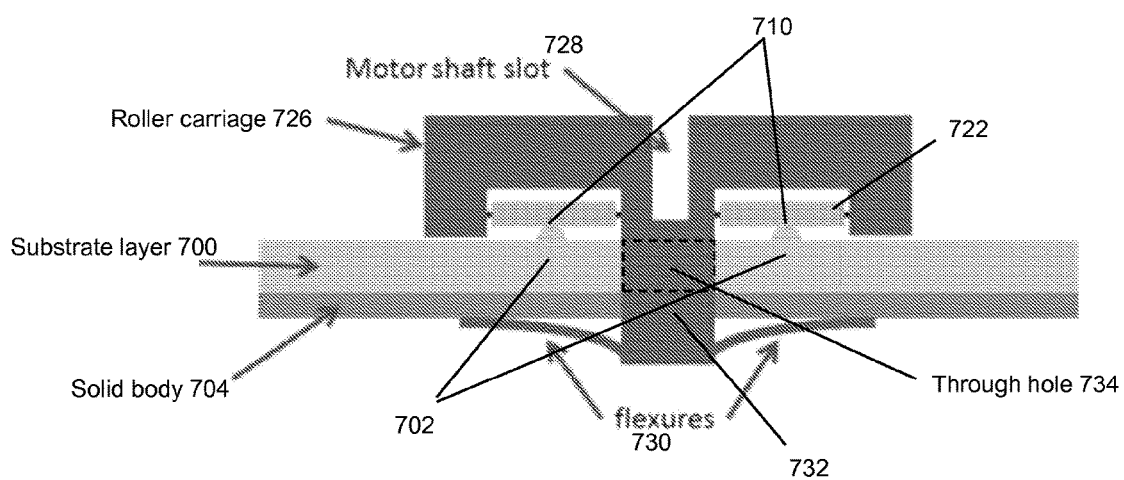
FIG. 7 is a schematic representation showing operation of one embodiment of a fluid-flow control device described herein, wherein a roller assembly is mechanically connected to the deformable portion of a disposable substrate (e.g., elastomeric), for example, e.g., using a coupler, wherein the disposable substrate is affixed to a solid body. The load concentrators formed on the top surface of the deformable portion of the substrate layer are in contact with the rolling elements configured to be engageable with a coupler (e.g., rolling elements placed in a roller carriage mechanically connected to a coupler). The coupler fits into a through-hole in the deformable portion of the substrate layer affixed to one side of a solid body and terminates in a flexure affixed to another side of the solid body. Pressing the coupler (which is mechanically connected to the roller assembly) against the flexure provides a spring force necessary for compression of the deformable portion of the substrate layer.

In some embodiments, a driving element (e.g., a motor) can be integrated into the actuator. In other embodiments, the actuator can be mechanically connected to a driving element, e.g., a motor such that at least a portion of the actuator can be detached from the driving element, e.g., a motor, if needed. For example, the actuator can comprise a detachable mechanical connector and/or adaptor, e.g., a motor shaft slot (728 as shown in FIG. 7), to provide detachable mechanical connection with a driving element, e.g., a motor.

Existing peristaltic pumps and/or valves, e.g., planar pumps, generally comprise non-disposable mechanical parts (e.g., but not limited to, driving elements such as motors, and rolling elements) and fluid-contacting parts integrated together in one assembly. Thus, there is no simple way to dispose of the fluid-contacting portion of the pumps while retaining the motor/mechanics without re-calibration. Accordingly, in some embodiments, the fluid-flow control device is configured to provide easy serviceability, e.g., the fluid-contacting component comprising, e.g., injection-moldable polymer components such as substrate layer, can be readily replaced and/or separated from the mechanical components. Some embodiments of the micropumps/microvalves described in the International Patent Application No. WO 2012/048261 do not readily support this functionality, since the bearings can fall out and calibration is done with weights and a manual set-screw.

For example, as shown in FIG. 5, the actuator 520 (comprising mechanical components, e.g., but not limited to, rolling elements and/or driving elements (e.g., a motor)) and the substrate layer 500 (fluid-contacting part) of the fluid-flow control device described herein can be configured to be detachable from each other. The actuator (including, e.g., motor and roller assembly) can be separated from at least the substrate layer comprising a deformable portion and a mechanism can be provided to operate two parts against each other in a simple serviceable manner. By way of example only, in some embodiments, at least the substrate layer can be aligned with respect to the actuator (including, e.g., motor and roller assembly) using, e.g., a frame and/or alignment pins, and the fluid-flow control device can further comprise a fastener element, e.g., a latch and/or a lever, to secure the substrate layer and the actuator together when the device is in use. In some embodiments, the substrate layer comprising the deformable portion can be disposable.

Rolling Elements Configured to be Coupled with a Deformable Portion of the Substrate Layer Prior to Use ("Snap-On Rolling Elements") (Feature (iii) of Table 1)

While in some embodiments, the rolling element(s) can be integrated into the actuator, which are then brought into contact with the deformable portion during operation, in alternative embodiments, referring to FIG. 7 as an example only, at least the top surface of the deformable portion 702 of substrate layer (or the top surface of the load concentrator 710 formed on the top surface of the deformable portion 702, if any) can be configured to be in pre-contact with at least one rolling element 722 described herein (feature (iii)), e.g., to form a "snap-on rolling element" for plug-and-play applications. In one embodiment, the snap-on rolling element can be integrated into a plug-and-play cartridge as described in the U.S. Application No. 61/856,876 filed Jul. 22, 2013; U.S. Provisional Application No. 61/696,997, filed on Sep. 5, 2012 and No. 61/735,215, filed on Dec. 10, 2012, contents of each application are incorporated herein by reference in their entireties.

Alternatively, these embodiments can be desirable for use as valves because it can retain the fluidic configuration even when it is not engaged with a driving element (e.g., a motor). In these embodiments, the rolling element(s) can be configured to be engageable with part of the actuator that is detachable from a driving element (e.g., a motor). In some embodiments, the rolling element(s) can be mechanically connected to a shaft fixed to the actuator, e.g., to prevent bearing-slip problem as described above.

Referring to FIG. 7, an assembly of rolling elements 722 can be mechanically connected to the deformable portion 702 (e.g., a flat deformable portion) or load concentrators 710 of a substrate layer 700 described herein (e.g., a disposable, elastomeric substrate), for example, e.g., using a coupler 732, wherein the substrate layer 700 can be affixed to a solid body 704. The load concentrators 710 formed on the top surface of the deformable portion 702 of the substrate layer 700 can be configured to be in contact with the rolling elements 722, which are configured to be engageable with a coupler 732 (e.g., rolling elements 722 placed in a roller carriage 726 mechanically connected to a coupler 732). The coupler 732 can fit into a through-hole 734 in the deformable portion 702 of the substrate layer 700 affixed to one side of a solid body 704 and terminates in a flexure material 730 affixed to another side of the solid body 704. The coupler 732 can grab on to the back of the solid body 704, e.g., with a fastener element (e.g., a screw or a clip). Pressing the coupler 732 (which is mechanically connected to the roller carrier 726 holding the rolling elements 722) against the flexure 730 can provide and/or attain an appropriate spring force necessary for compression of the deformable portion 702 of the substrate layer 700. In some embodiments, the coupler 732 can be pushed against the deformable portion 702 and load concentrators 710 (if any) to attain correct compression by the engaging driving element (e.g., a motor). Alternatively, the coupler 732 can be pushed against the deformable portion 702 and load concentrators 710 (if any) to attain correct compression, for example, by integrating a discrete spring; by incorporating a flexure material 730, e.g., placed at the back of the solid body 704; and/or by controlling the length of coupler 704 being pushed against the deformable portion 702 and load concentrators 710 (if any), to attain the correct strain.

Elastic Elements (Feature (v) of Table 1)

In some embodiments of various aspects described herein, the fluid-flow control device can comprise the feature (v), i.e., the actuator comprises at least one elastic element (including, e.g., at least 2, at least 3, at least 4 or more elastic elements) mechanically coupled to at least one or more (e.g., including, e.g., at least 2, at least 3, at least 4, at least 5, at least 6, at least 7, at least 8, at least 9, at least 10, or more) rolling elements. The elastic element (e.g., but not limited to, a spring or flexure) can be selected such that a small variation in displacement of the elastic element does not correspond to a large deviation in force. Thus, the presence of such elastic element can provide a better control of the compressive force (e.g., to about +/−5%) to the deformable portion of the substrate layer, even in the absence of calibration prior to use. Further, the presence of an elastic element can ensure a reliable compression of fluidic conduit(s) that is robust to alignment tolerances between the deformable portion and the actuator (including, e.g., the pump/valve roller assembly).

For example, in some embodiments, the elastic element can include a spring or any functional equivalent thereof. The spring or any functional equivalent thereof can be used in the coupling of a driving element (e.g., a motor) to the deformable portion of the substrate layer. In some embodiments, the spring can be selected such that the displacement of the spring is a small fraction of the spring's overall compressed length (so that force applied is relatively constant), or alternatively, in some embodiments, the spring can be pre-compressed such that the spring can be ready to provide a desired effectively near-constant force as soon as the deformable portion of the substrate layer comes into contact with the rolling elements and/or low-friction materials. Any art-recognized methods used to pre-compress a spring can be integrated into the fluid-flow control devices described herein. By way of example only, as shown in FIG. 5, any type of spring and/or flexure element 528 can be placed in the back of a driving element, e.g., a motor 530 and/or an assembly of rolling elements 522. In some embodiments, the spring or flexure element 528 can be pre-compressed by mechanically connecting to a rod structure (e.g., but not limited to, a shoulder bolt 532) such that the rod structure 532 pre-compresses the spring or flexure element 528.

In alternative embodiments, a flexure substrate, e.g., the substrate layer and/or the solid body itself being sufficiently flexible, can be used as an elastic element, for example, in place of a spring element. In some embodiments, as shown in FIG. 7, a separate flexure substrate 730 can be placed in the back of the solid body and used as an elastic element.

Embodiments of various aspects described herein can be defined in any of the following numbered paragraphs:

1. A fluid-flow control device comprising:
   a. a substrate layer comprising a deformable portion,
   b. one or more fluidic conduits disposed in the substrate layer, wherein at least one of the fluidic conduits comprises: an inlet portion for receiving a fluid, an outlet portion for outputting the fluid, and a central portion between the inlet portion and the outlet portion; and wherein the central portion comprises a pumping channel;
   c. at least one of the following features:
      i. the deformable portion including at least one load concentrator; wherein the load concentrator is aligned with the pumping channel;
      ii. the central portion further comprising at least one roll-off portion, wherein the roll-off portion includes a positive effective radius of curvature, as compared to a curvature of the pumping channel, whereby the roll-off portion gradually extends outside of a region of compression of the pumping channel; and
      iii. a top surface of the deformable portion being coupled to at least one rolling element.
2. A fluid-flow control device comprising:
   a. a substrate layer comprising a deformable portion, the deformable portion including a load concentrator;
   b. one or more fluidic conduits disposed in the substrate layer, wherein at least one of the fluidic conduits comprises: an inlet portion for receiving a fluid, an outlet portion for exiting the fluid, and a central portion between the inlet portion and the outlet portion; and wherein the central portion comprises a pumping channel, the pumping channel being aligned with the load concentrator such that a pressure applied to the load concentrator can cause the pumping channel to deform.
3. The device of paragraph 2, wherein the central portion further comprises at least one roll-off portion, wherein the roll-off portion includes a positive effective radius of curvature, as compared to a curvature of the pumping channel, whereby the roll-off portion gradually extends outside of a region of compression of the pumping channel.
4. The device of paragraph 3, wherein the effective radius of curvature includes a combination of radii of curvature when the roll-off portion is not a circular arc.
5. The device of paragraph 4, wherein the radii of curvature is measured from a centerline of the roll-off portion.
6. The device of paragraph 4, wherein the radii of curvature is measured from an inner boundary of the roll-off portion.
7. The device of paragraph 4, wherein the radii of curvature is measured from an outer boundary of the roll-off portion.
8. The device of any of paragraphs 1-7, wherein when the inlet portion and the outlet portion are placed outside an outer boundary of the region of compression of the pumping channel, the effective radius of curvature of the roll-off portion is larger than the radius of curvature of the pumping channel (excluding the effective radius of curvature of infinity).
9. The device of any of paragraphs 1-7, wherein when at least one of the inlet portion and the outlet portion is circumscribed by an outer boundary of the region of compression of the pumping channel, the effective radius of curvature of the roll-off portion is no more than 50% of the radius of curvature of the pumping channel.
10. The device of any of paragraphs 1-9, wherein the roll-off portion is placed between the inlet portion and the pumping channel.
11. The device of any of paragraphs 1-9, wherein the roll-off portion is placed between the outlet portion and the pumping channel.
12. The device of any of paragraphs 1-9, wherein the at least one roll-off portion comprises a first roll-off portion between the inlet portion and the pumping channel, and a second roll-off portion between the outlet portion and the pumping channel.
13. The device of any of paragraphs 1-12, wherein the load concentrator is formed of a material substantially same as that of the deformable portion.
14. The device of any of paragraphs 1-12, wherein the load concentrator is formed of a material different from that of the deformable portion.
15. The device of paragraph 14, wherein the material forming the load concentrator is less deformable than the material forming the deformable portion.
16. The device of paragraph 14 or 15, wherein the material forming the deformable portion comprises polydimethylsiloxane (PDMS), polymethylmethacrylate (PMMA), polyurethane, styrene-ethylene-butylene-styrene (SEBS), polypropylene, polycarbonate, polyester, or any combinations thereof.
17. The device of paragraph 14 or 15, wherein the material forming the load concentrator comprises silicone rubber, natural rubber, nitrile rubber, polydimethylsiloxane (PDMS), polyurethane, rubber, gels, hydrogels, molded plastic, polymethylmethacrylate (PMMA), polycarbonate, polytetrafluoroethylene (e.g., TEFLON™), polyvinylchloride (PVC), polysulfone, mixture of hydrocarbon oils, polymers containing plasticizers, synthetic polyisoprene, polybutadiene, chloroprene rubber, polychloroprene, neoprene, baypren, butyl rubber, halogenated butyl rubbers, styrene-butadiene rubber, styrene-ethylene/butadiene-styrene (SEBS), hydrogenated nitrile rubbers, ethylene propylene rubber, ethylene propylene diene monomer (EPDM) rubber, epichlorohydrin rubber, polyacrylic rubber, fluorosilicone rubber, fluoroelastomers, perfluoroelastomers, polyether block amides, chlorosulfonated polyethylene, ethylene-vinyl acetate, thermoplastic elastomers (TPE) and any combinations thereof.
18. The device of any of paragraphs 1-17, wherein the load concentrator is formed on a top surface of the deformable portion.
19. The device of any of paragraphs 1-17, wherein at least a portion of the load concentrator is embedded below a top surface of the deformable portion.
20. The device of any of paragraphs 1-19, wherein the load concentrator has a cross-section of a circle, a semi-circle, an oval, a square, a rectangle, a polygon, an irregular shape or any combinations thereof.
21. The device of any of paragraphs 1-20, wherein the load concentrator is a ring comprising a protruding surface.
22. The device of any of paragraphs 1-21, wherein the load concentrator is a ring comprising a rounded convex surface.
23. The device of any of paragraphs 1-22, further comprising an actuator configured to be engageable with the top surface of the deformable portion, thereby deforming the pumping channel and forcing the fluid to move through the central portion from the inlet portion to the outlet portion as the actuator applies a pressure to the top surface of the deformable portion.
24. The device of paragraph 23, wherein the actuator comprises at least one rolling element.
25. The device of paragraph 24, wherein the at least one rolling element comprises ball bearings, plain bearings (e.g., sleeve bearings), roller bearings (e.g., cylindrical rollers, needles, tapered rollers, spherical rollers), or any combinations thereof.
26. The device of any of paragraphs 24-25, wherein the at least one rolling element comprises a rounded (convex) roller.
27. The device of any of paragraphs 24-25, wherein the at least one rolling element is cylindrical, tapered, convex, spherical, irregular-shaped, or a combination thereof.
28. The device of any of paragraphs 24-27, wherein the at least one rolling element is mechanically connected to a shaft fixed to the actuator.
29. The device of any of paragraphs 23-28, wherein the actuator comprises a low friction material capable of sliding against the deformable region of the substrate layer.
30. The device of paragraph 29, wherein the low friction material comprises polytetrafluoroethylene (PTFE), acetal, DELRIN®, RULON®, or any combinations thereof.
31. The device of any of paragraphs 23-30, wherein the actuator further comprises an elastic element (e.g., spring or flexure) mechanically coupled to the at least one rolling element, whereby the elastic element controls a compression force of the rolling element applied to the load concentrator.

32. The device of paragraph 31, wherein the elastic element is configured to be pre-compressed.

33. The device of paragraph 32, wherein pre-compressed elastic element is mechanically connected to a rod structure such that the rod structure pre-compresses the elastic element.

34. The device of paragraph 33, wherein the rod structure comprises a shoulder bolt or a functional equivalent thereof.

35. The device of any of paragraphs 1-34, wherein a top surface of the deformable portion is coupled to at least one rolling element.

36. The device of paragraph 35, wherein said at least one rolling element is configured to be engageable with the actuator to deform the deformable portion.

37. The device of any of paragraphs 1-36, wherein the load concentrator has a height of about 10 µm to about 10 mm, or about 30 µm to about 6 mm, or about 1 mm.

38. The device of any of paragraphs 1-37, wherein at least the deformable portion of the substrate layer has a thickness of about 10 µm to about 10 mm, or about 30 µm to about 6 mm, or about 1 mm.

39. The device of any of paragraphs 1-38, wherein at least a portion of the central portion of said one or more fluidic conduits are defined in a bottom surface of the deformable portion.

40. The device of any of paragraphs 1-38, wherein at least the central portion of said one or more fluidic conduits are defined between the top surface and the bottom surface of the deformable portion.

41. The device of any of paragraphs 1-40, wherein the deformable portion is disposed on a solid body.

42. The device of paragraph 41, wherein at least a portion of the central portion of the fluidic conduit is defined in a top surface of the solid body.

43. The device of any of paragraphs 1-42, wherein at least one of the fluidic conduits forms at least one rounded surface.

44. The device of any of paragraphs 1-43, wherein at least one of the fluidic conduits comprises a surface forming a contact angle of about 50 degrees to about 70 degrees relative to a bottom boundary of the fluidic conduit.

45. The device of any of paragraphs 23-44, wherein the substrate layer and the actuator are detachable from each other.

46. The device of paragraph 45, wherein the substrate layer comprising the deformable portion is disposable.

47. The device of paragraph 45 or 46, further comprising a spring, a latch or a lever to secure the substrate layer and the actuator together when the device is in use.

48. The device of any of paragraphs 23-47, wherein the actuator further comprises a driving element (e.g., a motor).

49. The device of any of paragraphs 1-48, wherein at least one of the fluidic conduits is a microfluidic channel.

50. The device of any of paragraphs 1-49, wherein the device is configured to be a pumping device.

51. The device of any of paragraphs 1-50, wherein the device is configured to be a valve device.

52. A fluid-flow control device comprising:
   a. a substrate layer comprising a deformable portion,
   b. one or more fluidic conduits disposed in the substrate layer, wherein at least one of the fluidic conduits comprises: an inlet portion for receiving a fluid, an outlet portion for outputting the fluid, and a central portion between the inlet portion and the outlet portion; and wherein the central portion comprises a pumping channel;
   c. an actuator having at least one rolling element in contact with the deformable portion and an elastic element adapted to cause the at least one rolling element to apply a compressive force on the deformable portion.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims. The invention is described with respect to an orientation of the embodiments wherein the deformable portion is positioned on the top of the device, however, it is within the scope of the invention that the device can be inverted whereby the deformable portion or the load concentrator is positioned on the bottom of the device as shown in FIGS. 5 and 9C.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A method of controlling fluid flow, comprising:
   a) providing
      i) a disposable cartridge that holds a microfluidic device, said cartridge comprising an elastomeric manifold, said manifold comprising a deformable portion affixed to a first side of a solid body;

ii) a fluidic conduit configured to be in contact with the deformable portion, said fluidic conduit comprising fluid, an inlet for introduction of said fluid, an outlet for exit of said fluid, and a central portion between the inlet and the outlet, said fluidic conduit in fluidic communication with said microfluidic device; and iii) an actuator comprising an elastic element that is present on a second side of said solid body and that is mechanically coupled to a rolling element, said rolling element configured to engage said deformable portion of said elastomeric manifold;

b) engaging said deformable portion of said elastomeric manifold with said rolling element so as to deform the deformable portion, whereby said fluid is forced to move through the central portion of said fluidic conduit and into said microfluidic device, thereby controlling fluid flow; and c) disengaging the deformable portion from the rolling element.

2. The method of claim 1, further comprising, d) disposing of said cartridge.

3. The method of claim 1, wherein said rolling element is mechanically connected to a shaft fixed to said actuator.

4. The method of claim 1, wherein the microfluidic device is an organ-on-a-chip microfluidic device comprising a membrane with cells.

5. The method of claim 1, wherein the outlet of the fluidic conduit is adaptably connected to the microfluidic device.

6. The method of claim 1, wherein the elastic element is a spring or flexure.

7. The method of claim 1, wherein the actuator further comprises a rod structure mechanically coupled to the elastic element.

8. The method of claim 1, wherein said rolling element engages said deformable portion of said elastomeric manifold in step b) via a load concentrator.

9. The method of claim 8, wherein said load concentrator is on the top surface of the deformable portion and in contact with the rolling element.

10. A method of controlling fluid flow, comprising:
a) providing a fluid-flow control device comprising
i) a body that holds a microfluidic device, said body comprising a detachable elastomeric manifold, said manifold comprising a deformable portion affixed to a first side of a solid body, and ii) a fluidic conduit configured to be in contact with the deformable portion, said fluidic conduit comprising fluid, an inlet for introduction of said fluid, an outlet for exit of said fluid, and a central portion between the inlet and the outlet, said fluidic conduit in fluidic communication with said microfluidic device; and iii) an actuator comprising an elastic element that is present on a second side of said solid body and that is mechanically coupled to a rolling element, said rolling element configured to engage said deformable portion of said elastomeric manifold;

b) engaging said deformable portion of said elastomeric manifold with said rolling element so as to deform the deformable portion, whereby said fluid is forced to move through the central portion of said fluidic conduit and into said microfluidic device, thereby controlling fluid flow; and c) disengaging the deformable portion from the rolling element.

11. The method of claim 10, further comprising, disposing of said detachable elastomeric manifold.

12. The method of claim 11, further comprising, prior to said disposal, detaching said detachable elastomeric manifold from said body.

13. The method of claim 12, further comprising attaching a second elastomeric manifold to said body.

14. The method of claim 10, wherein said body comprises a cartridge that holds a microfluidic device.

15. The method of claim 10, wherein the outlet of the fluidic conduit is adaptably connected to the microfluidic device.

16. The method of claim 10, wherein said microfluidic device is an organ-on-a-chip device comprising a membrane with cells.

17. The method of claim 10, wherein the elastic element is a spring or flexure.

18. The method of claim 10, wherein the actuator further comprises a rod structure mechanically coupled to the elastic element.

19. The method of claim 10, wherein said rolling element engages said deformable portion of said elastomeric manifold in step b) via a load concentrator.

20. The method of claim 19, wherein said load concentrator is on the top surface of the deformable portion and in contact with the rolling element.

* * * * *